(12) United States Patent
Myers

(10) Patent No.: US 7,613,489 B2
(45) Date of Patent: Nov. 3, 2009

(54) OPTIMIZED WAVELENGTH GAP FOR IMPROVED STO2 MEASUREMENT

(75) Inventor: Dean E. Myers, Stewart, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 753 days.

(21) Appl. No.: 11/131,698

(22) Filed: May 18, 2005

(65) Prior Publication Data

US 2005/0277818 A1    Dec. 15, 2005

Related U.S. Application Data

(60) Provisional application No. 60/572,220, filed on May 18, 2004.

(51) Int. Cl.
*A61B 5/1455* (2006.01)
(52) U.S. Cl. ..................................... 600/323
(58) Field of Classification Search ............... 128/633; 600/310, 322, 323, 473, 476
See application file for complete search history.

(56) References Cited

U.S. PATENT DOCUMENTS

| | | | |
|---|---|---|---|
| 5,879,294 A * | 3/1999 | Anderson et al. | 600/310 |
| 6,377,840 B1 | 4/2002 | Gritsenko et al. | |
| 6,473,632 B1 * | 10/2002 | Myers | 600/322 |
| 6,481,899 B1 | 11/2002 | Quast et al. | |
| 6,487,343 B1 | 11/2002 | Lewandowski et al. | |
| 6,667,803 B1 | 12/2003 | Flessland et al. | |

FOREIGN PATENT DOCUMENTS

WO    WO 00/77495    12/2000

OTHER PUBLICATIONS

Jeon et al., Non-invasive total hemoglobin measurement, Jan. 2002, Journal of Biomedical Optics ,7(1), 45-50.*
Cooper et al., "The Noninvasive Measurement of Absolute Cerebral Deoxyhemoglobin Concentration and Mean Optical Path Length in the Neonatal Brain by Second Derivative Near Infrared Spectroscopy", *Pediatric Research*, Jan. 1996, pp. 32-38, vol. 39, No. 1.
Binzoni et al., "Energy Metabolism and Interstitial Fluid Displacement in Human Gastrocnemius During Short Ischemic Cycles", *Journal of Applied Physiology*, Oct. 1998, pp. 1244-1251, vol. 85, No. 4, American Physiological Society, Bethesda, MD.
Chance et al., "Phase Measurement of Light Absorption and Scatter in Human Tissue", *Review of Scientific Instruments*, Oct. 1998, pp. 3457-3481, vol. 69, No. 10, American Institute of Physics.
Colier et al., "A Comparative Study of Two Near Infrared Spectrophotometers for the Assessment of Cerebral Haemodynamics", *Oxygen, Carbon Dioxide, and Electrolytes in Critical Care: Proceedings of the Workshop on Oxygen, Carbon Dioxide, and Electrolytes in Critical Care held in* Copenhagen, Denmark, Jan. 26-27, 1995, pp. 101-105, Acta Anaesthesiologica Scandinavica, Supplementum 107, vol. 39.

(Continued)

*Primary Examiner*—Eric F Winakur
*Assistant Examiner*—Ahmed Elhassan
(74) *Attorney, Agent, or Firm*—Faegre & Benson LLP

(57) ABSTRACT

A method and system for producing improved more accurate measurements of oxyhemoglobin levels in tissue when measured using near infrared spectroscopy (NIRS). Light sources and processing methods are selected to such that the effects of a confounding chromophore in the tissue under study are minimized.

29 Claims, 16 Drawing Sheets

OTHER PUBLICATIONS

Cui et al., "Experimental Study of Migration Depth for the Photons Measured at Sample Surface", *SPIE*, 1991, pp. 180-191, vol. 1431.

De Blasi et al., "Noninvasive Measurement of Forearm Blood Flow and Oxygen Consumption by Near-Infrared Spectroscopy", *Journal of Applied Physiology*, Mar. 1994, pp. 1388-1393, vol. 76, No. 3, American Physiological Society, Bethesda, MD.

Delpy et al., "Quantification in Tissue Near-Infrared Spectroscopy", *Phil Trans R Soc Lond, B*, 1997, pp. 649-659, vol. 352, The Royal Society.

Fantini et al., "Cerebral and Muscle Oxygen Saturation Measurement by Frequency-Domain Near-Infra-Red Spectrometer", *Medical & Biological Engineering & Computing*, Mar. 1995, pp. 228-230, vol. 33, No. 2.

Ferrari et al., "Noninvasive Determination of Hemoglobin Saturation in Dogs by Derivative Near-Infrared Spectroscopy", *American Journal of Physiology*, May 1989, pp. H1493-H1499, vol. 256, No. 5, Part 2, American Physiological Society, Bethesda, MD.

Franceschini et al., "Near-Infrared Absorption and Scattering Spectra of Tissues in Vivo", *Pro. SPIE*, 1999, pp. 526-531, vol. 3597.

Hoofd et al., "A Modeling Investigation to the Possible Role of Myoglobin in Human Muscle in Near Infrared Spectroscopy (NIRS) Measrements", *Oxygen Transport to Tissue XXIV*, 27th Annual meeting of the International Society on Oxygen Transport to Tissue (ISOTT), held at Dartmouth Medical School, Hanover, NH, Aug. 28-Sep. 2, 1999, pp. 637-643, © 2003, Plenum Publishers, New York.

Lefevre et al., "Determination of Plasma Protein-Bound Malondialdehyde by Derivative Spectrophotometry", *European Journal of Clinical Chemistry and Clinical Biochemistry*, Aug. 1996, pp. 631-636, vol. 34, No. 8, Walter de Gruyter, Berlin, NY.

Matcher et al., "Performance Comparison of Several Published Tissue Near-Infrared Spectroscopy Algorithms", *Analytical Biochemistry*, May 1995, pp. 54-68, vol. 227, No. 1, Academic Press, Inc., Harcourt Brace & Co., San Diego, New York, Boston, London, Sydney, Tokyo, Toronto.

Merrick et al., "Evaluation of Absorption and First- and Second-Derivative Spectra for Simultaneous Quantification of Bilirubin and Hemoglobin", *Clinical Chemistry*, 1986, pp. 598-602, vol. 32, No. 4.

Punwani et al., "MRI Measurements of Cerebral Deoxyhaemoglobin Concentration [dHB]—Correlation With Near Infrared Spectroscopy (NIRS)", *NMR In Biomedicine*, Oct. 1998, pp. 281-289, vol. 11, No. 6, John Wiley & Sons, Ltd.

Simpson et al., "Near-Infrared Optical Properties of Ex Vivo Human Skin and Subcutaneous Tissues Measured Using the Monte Carlo Inversion Technique", *Phys Med Biol*, Sep. 1998, pp. 2465-2478, vol. 43, No. 9, IOP Publishing Ltd, UK.

Skov et al., "Estimation of Cerebral Venous Saturation in Newborn Infants by Near Infrared Spectroscopy", *Pediatric Research*, 1993, pp. 52-55, vol. 38, No. 1.

Tuchin, "Optical Properties of Tissues with Strong (Multiple) Scattering", *Tissue Optics: Light Scattering Methods and Instruments for Medical Diagnosis*, 2000, pp. 98-108, SPIE, USA.

Visser et al., "Density of Fat-Free Body Mass: Relationship with Race, Age, and Level of Body Fatness", *American Journal of Physiology*, May 1997, pp. E781-E787, vol. 272, No. 5, Part 1, The American Physiological Society, Bethesda, MD.

Yoxall et al., "Measurement of Cerebral Venous Saturation By Near Infrared Absorption Spectroscopy", *Pediatric Research*, Dec. 1994, p. 45 A (1 pg.), vol. 36, No. 6.

\* cited by examiner

Table 1. Predicted %StO₂ Error for different confounding chromophore attenuation conditions.

| A | B | C | D | E | F = (B+C)/(D+E) | G | H |
|---|---|---|---|---|---|---|---|
| Examples | Numerator Interfering Chromophore Bias | Numerator 2nd Derivative Attenuation | Denominator Interfering Chromophore Bias | Denominator 2nd Derivative Attenuation | Ratio of Combined 2nd Derivative Attenuation | Predicted %StO₂ from Column F using Fig. 8A | %StO₂ Error |
| 1 | 0 | 0.15 | 0 | -0.10 | -1.5 | 60% | 0 |
| 2 | +0.05 | 0.20 | +0.05 | -0.05 | -4.0 | 95% | +35% |
| 3 | -0.05 | 0.10 | -0.05 | -0.15 | -0.67 | 0% | -60% |
| 4 | +0.05 | 0.20 | -0.03 | -0.13 | -1.53 | 62% | +2% |
| 5 | -0.05 | 0.10 | +0.03 | -0.07 | -1.42 | 57% | -3% |

Table II

Lambert-Beer Equation Spectrum Results

| SO₂ (%) | Hbt (mM) | Path (cm) | Deriv. 720nm | Deriv. 760nm | Deriv Scaled |
|---|---|---|---|---|---|
| 0 | 0.05 | 1 | 0.070 | -0.054 | -1.29 |
| 0 | 0.50 | 1 | 0.703 | -0.545 | -1.29 |
| 25 | 0.05 | 1 | 0.055 | -0.040 | -1.35 |
| 25 | 0.50 | 1 | 0.546 | -0.404 | -1.35 |
| 50 | 0.05 | 1 | 0.039 | -0.026 | -1.48 |
| 50 | 0.50 | 1 | 0.389 | -0.263 | -1.48 |
| 75 | 0.05 | 1 | 0.023 | -0.012 | -1.89 |
| 75 | 0.50 | 1 | 0.232 | -0.123 | -1.89 |
| 96 | 0.05 | 1 | 0.010 | 0.000 | -22.10 |
| 96 | 0.50 | 1 | 0.100 | -0.005 | -22.10 |
| 0 | 0.05 | 10 | 0.703 | -0.545 | -1.29 |
| 0 | 0.50 | 10 | 7.030 | -5.446 | -1.29 |
| 25 | 0.05 | 10 | 0.546 | -0.404 | -1.35 |
| 25 | 0.50 | 10 | 5.459 | -4.039 | -1.35 |
| 50 | 0.05 | 10 | 0.389 | -0.263 | -1.48 |
| 50 | 0.50 | 10 | 3.888 | -2.633 | -1.48 |
| 75 | 0.05 | 10 | 0.232 | -0.123 | -1.89 |
| 75 | 0.50 | 10 | 2.317 | -1.227 | -1.89 |
| 96 | 0.05 | 10 | 0.100 | -0.005 | -22.10 |
| 96 | 0.50 | 10 | 0.997 | -0.045 | -22.10 |

OPTIMIZED WAVELENGTH GAP FOR IMPROVED STO2 MEASUREMENT

CROSS-REFERENCE TO RELATED APPLICATIONS

This application claims priority to U.S. Provisional Patent Application No. 60/572,220, filed May 18, 2004, which is included herein by reference.

BACKGROUND OF THE INVENTION

A goal of in vivo Near Infrared Reflectance Spectroscopy ["NIRS"] is to provide a reliable and accurate noninvasive quantification of oxyhemoglobin concentration [$HbO_2$], deoxyhemoglobin concentration [Hb], total hemoglobin concentration [$HbO_2$+Hb] and/or tissue hemoglobin oxygen saturation [$HbO_2$]/[$HbO_2$+Hb] in a tissue environment where measured light photons, 650 nm to 1000 nm for example, are numerously scattered along their propagation paths. In vivo NIRS instruments use reflectance mode probes to measure scattered light remitted at some distance from where the light is emitted into the tissue. This probe spacing distance weights the measured attenuated light signal to hemoglobin absorption occurring below the tissue surface.

Continuous wave (CW) spectrometers measure changes in the attenuation of 2-6 wavelengths of light, allowing algorithms based on a modified Beer-Lambert law to provide good estimates of changes in the tissue concentration of HHb and $HbO_2$, (measured in micromoles chromophore per ml of tissue interrogated by the NIR light). However, the ultimate goal of tissue near infrared spectroscopy is the measurement of absolute chromophore concentrations. This requires additional information. This can occasionally be gained by physiological manipulation e.g. head tilting, venous occlusion, arterial occlusion and slow or rapid changes in the inspired oxygen fraction. Under appropriate conditions these methods allow for the calculation of the flow of hemoglobin into tissue, the rate of removal of oxygen from hemoglobin and the oxygenation state of hemoglobin entering specific compartments. Suitable calculations (with relatively few a priori assumptions) can then be used to measure such physiological parameters as blood flow, blood volume, venous saturation and tissue oxygen consumption.

It is also possible to gain the additional information required to calculate absolute chromophore concentrations by the use of more sophisticated measurement systems. Time resolved (TRS) instruments use pulsed lasers with synchronized detection in order to resolve the amount of time that launched photons remain in tissue, picoseconds, before being detected. Phase resolved (PMS) instruments modulate the intensity of emitted light at a MHz frequency in order to relate a phase shift between emitted and detected signals to the average amount of time, and hence distance, that photons travel within tissue. For both methods either a time domain or frequency domain solution to a diffusion theory equation allows an estimate of the tissue absorption coefficient, $\mu_a$. Once a tissue absorption coefficient is known for the wavelengths of emitted light, the concentration of the significant absorbers can be determined.

Multiple source detector separations have also been used to generate additional information. In the simplest designs two detectors are spatially separated, one close to the source (e.g. 2 cm) and one more distant (e.g. 4 cm). The assumption is then made that the additional light attenuation due to the longer separation comes only from deep tissue and that traveling the shorter path includes significant information from surface chromophores (e.g. in the skin or skull). The difference between the two then yields information about the absolute tissue chromophore concentration. Such methods (predominantly used to resolve problems in adult brain measurements) have met with only limited success. However, recently more sophisticated CW instruments have been developed using spatially resolved spectroscopy (SRS) to quantify NIRS signals representative of tissue hemoglobin oxygen saturation and total hemoglobin concentration. SRS measures an attenuated light signal at multiple probe spacing distances to solve for tissue absorption using an assumed or calibrated value for transport tissue scattering coefficient, $\mu_s'$, using diffusion theory equations. Additionally, a phase resolved method has been combined with the multi-distance approach to provide a measured estimate of $\mu_s'$ and estimates of tissue hemoglobin oxygen saturation and total hemoglobin concentration.

While all these methods yield apparent values for tissue chromophore concentrations, there have been relatively few attempts to compare and/or cross-validate, one against the other. The mean values of resting hemoglobin saturation can vary between methods; direct comparisons sometimes, but not always give similar readings. Tissue absorbers which exhibit non-linear absorption and overlap the measured wavelength region can confound measurement accuracy for the desired analyte. The degree of measurement inaccuracy would depend upon the relative amounts of the interfering and analyte chromophores and their characteristic absorbance magnitude at each measured wavelength (absorption coefficient).

Water has a non-linear spectral attenuation in the wavelength region of 680 to 800 nm that is amplified due to its high concentration in tissue, 70 wt % or 43 M considering lean tissue density of 1.1 Kg/L. It is desirable to limit the amount of chromophore interference (i.e. water) from an analyte chromophore measurement (i.e. % $StO_2$).

Many publications have been devoted to measurement of tissue attributes using NIRs including, Anderson D L, Houk G L, Lewandowski M S, Myers D E and Ortner J P, *Tissue chromophore measurement system*, U.S. Pat. No. 5,879,294 March 1999; Binzoni T, Quaresima V, Barattelli G, Hiltbrand E, Gurke L, Terrier F, Cerretelli P and Ferrari M, Energy metabolism and interstitial fluid displacement in human gastrocnemius during short ischemic cycles, *J Appl Physiol* 85: 1244-51, 1998; Chance B, Cope M, Gratton E, Ramanujam N and Tromberg B, Phase measurement of light absorption and scatter in human tissue, *Review of Scientific Instrumentation*, 69: 3457-81, 1998; Colier W N, van Haaren N J and Oeseburg B, A comparative study of two near infrared spectrophotometers for the assessment of cerebral haemodynamics, *Acta Anaesthesiol Scand Suppl* 107: 101-5, 1995; Cooper C E, Elwell C E, Meek J H, Matcher S J, Wyatt J S, Cope M and Delpy D T, Noninvasive measurement of absolute cerebral deoxyhemoglobin concentration and mean optical path length in the neonatal brain by second derivative near infrared spectroscopy, The, *Pediatric Res* 39: 32-8, 1996; Cui W, Kumar C and Chance B, Experimental study of migration depth for the photons measured at sample surface, *Proc SPIE* 1431: 180-91, 1991; De Blasi R A, Fantini S, Franceschini M A, Ferrari M and Gratton E; Cerebral and muscle oxygen saturation measurement by frequency-domain near-infra-red spectrometer, *Med Biol Eng Comput* 33: 228-30, 1995; De Blasi R A, Ferrari M, Natali A, Conti G, Mega A and Gasparetto A, Noninvasive measurement of forearm blood flow and oxygen consumption by near-infrared spectroscopy, *J Appl Physiol* 76: 1388-93, 1994; Delpy D T and Cope M, Quantification in tissue near-infrared spectroscopy, *Phil*

Trans R Soc Lond 352: 649-59, 1997; Ferrari M, Wilson D A, Hanley D F, Hartmann J F, Rogers M C and Traystman R J, Noninvasive determination of hemoglobin saturation in dogs by derivative near-infrared spectroscopy, *Am J Physiol* 256: H1493-9, 1989; Flessland L D, Gritsenko S I, Lewandowski M S and Myers D E, Calibration mode recognition and calibration algorithm for spectrophotometric instruments, U.S. Pat. No. 6,667,803, December 2003; Franceschini M A, Gratton E, Hueber D and Fantini S, Near-infrared absorption and scattering spectra of tissues in vivo. *Pro. SPIE* 3597: 526-31, 1999; Gritsenko S I, Lewandowski M S and Myers D E, Signal acquisition and processing system for reduced output signal drift in a spectrophotometric instrument, U.S. Pat. No. 6,377,840, April 2002; Gritsenko S I, Lewandowski M S, Myers D E, Quast K R and Schmidt M A Optical connector latching mechanism for a spectrophotometric instrument 6,481,899, November 2002; Hoofd L, Colier W and Oeseburg B, A modeling investigation to the possible role of myoglobin in human muscle in near infrared spectroscopy (NIRS) measurements, *Adv Exp Med Biol* 530: 637-43, 2003; Lefevre G, Bonneau C, Rahma S, Chanu B, Brault D, Couderc R and Etienne J, Determination of plasma protein-bound malondialdehyde by derivative spectrophotometry, *Eur J Clin Chem Clin Biochem* 34, 631-6, 1996; Lewandowski M S, Quast K R, Myers D E and Schmidt M A, Fiber optic light mixer, U.S. Pat. No. 6,487,343 November 2002; Matcher S J, Elwell C E, Cooper C E, Cope M and Delpy D T, Performance comparison of several published tissue near-infrared spectroscopy algorithms, *Anal Biochem* 227: 54-68, 1995; Mayhew J, Johnston D, Berwick J, Jones M, Coffey P and Zheng Y, Evaluation of absorption and first and second derivative spectra for simultaneous quantification of bilirubin and hemoglobin *Clin. Chem.* 32: 598-602, 1986; Punwani S, Ordidge R J, Cooper C E, Amess P and Clemence M, MRI measurements of cerebral deoxyhaemoglobin concentration, *NMR Biomed* 11: 281-9, 1998; Simpson C R, Kohl M, Essenpreis M and Cope M, Near-infrared optical properties of ex vivo human skin and subcutaneous tissues measured using the Monte Carlo inversion technique, *Phys Med Biol* 43: 2465-78, 1998; Skov L, Pryds O, Greisen G and Lou H, Estimation of cerebral venous saturation in newborn infants by near infrared spectroscopy, *Pediatr Res* 33: 52-5, 1993; Visser M, Gallagher D, Deurenberg P, Wang J, Pierson R N Jr and Heymsfield S B, Density of fat-free body mass: relationship with race, age, and level of body fatness, *Am J Physiol* 272: E781-7, 1997; and Yoxall C W, Weindling A M, Dawani N M H and Peart I, Measurement of cerebral venous saturation by near infrared absorption spectroscopy, *Pediatr Res* 36: 45A, 1994.

Still, a need exists for a NIR instrument that reduces the effects of a confounding chromophore on the output signal value.

SUMMARY OF THE INVENTION

The disclosed method and apparatus provide improved tools for measurement of hemoglobin concentrations in tissue using NIRS. The invention relates specifically to an algorithm method and apparatus which relates a scaled (ratioed) 2nd derivative attenuation measurement to in vivo hemoglobin oxygen saturation (% $StO_2$). A 2nd derivative transformation of tissue attenuation measurements (2nd derivative spectroscopy) removes both baseline offset and linear slope from optical density attenuation spectra and provides a degree of robustness to the effects of wavelength dependent scattering. Another benefit of 2nd derivative spectroscopy is that tissue absorbers having near constant or linear absorption (over a chosen wavelength region) do not interfere with measurement of a desired analyte chromophore which exhibits significant non-linear wavelength dependent absorption.

The disclosed method describes how to optimize the wavelength gap used for calculating a 2nd derivative tissue attenuation measurement in order to reduce and/or eliminate the spectral influence of a confounding (interfering) chromophore on a desired analyte chromophore measurement. The method specifically relates to an analyte chromophore measurement that is correlated to the ratio of two distinct 2nd derivative attenuation measurements. The gap interval may be uniform or non-uniform (transformed) and can be similar or different between the chosen numerator and denominator 2nd derivative attenuation wavelengths. A common result of the gap interval optimization is that the spectral features of the interfering chromophore nearly equally affect the two 2nd derivative attenuation measurements and do not significantly affect the scaled (ratioed) 2nd derivative attenuation measurement which directly correlates to the measured analyte chromophore.

In one embodiment, the invention is a method for determining the level of hemoglobin oxygenation in tissue, that starts with illuminating the tissue under study using light having at least the wavelengths of approximately 692 nm, 720 nm, 732 nm, 748 nm, 760 nm and 788 nm. The light that has passed through a portion of the tissue is then sensed at a predetermined distance from the source of the illumination using a light detector. A value of the attenuation of light by the tissue at each of wavelengths of illumination of the tissue is then determined. Next, a second derivative value of the light attenuation at 720 nm through the equation (Second Derivative Attenuation)$_{720}$=Attenuation$_{748}$−2(Attenuation$_{720}$)+Attenuation$_{692}$ is determined. A second derivative value of the light attenuation at 760 nm through the equation (Second Derivative Attenuation)$_{760}$=Attenuation$_{788}$−2(Attenuation$_{760}$)+Attenuation$_{732}$ is also determined. Then, a scaled (Second Derivative Attenuation)$_{720}$ value is determined as a function of the (Second Derivative Attenuation)$_{720}$ divided by the (Second Derivative Attenuation)$_{760}$. Lastly, the scaled (Second Derivative Attenuation)$_{720}$ is compared to stored data relating hemoglobin oxygenation to the scaled (Second Derivative Attenuation)$_{720}$ to determine a hemoglobin oxygenation percentage.

In another embodiment, a method for determining the level of hemoglobin oxygenation in tissue, starts with illuminating the tissue under study using light having at least the wavelengths of approximately 680 nm, 720 nm, 732 nm, 760 nm and 788 nm. Light that has passed through a portion of the tissue is then sensed at a predetermined distance from the source of the illumination. A value of attenuation of light at each of wavelengths of illumination of the tissue is then determined. Next, a second derivative value of the light attenuation at 720 nm is determined through the equation (Second Derivative Attenuation)$_{720}$=Attenuation$_{760}$−2(Attenuation$_{720}$)+Attenuation$_{680}$. A second derivative value of the light attenuation at 760 nm is calculated through the equation (Second Derivative Attenuation)$_{760}$=Attenuation$_{788}$−2(Attenuation$_{760}$)+Attenuation$_{732}$. A scaled (Second Derivative Attenuation)$_{720}$ value is then determined as a function of the (Second Derivative Attenuation)$_{720}$ divided by the (Second Derivative Attenuation)$_{760}$. Lastly, the scaled (Second Derivative Attenuation)$_{720}$ is compared to stored data relating hemoglobin oxygenation to the scaled (Second Derivative Attenuation)$_{720}$ to determine a hemoglobin oxygenation percentage.

In yet another embodiment, a method for determining the level of hemoglobin oxygenation in tissue, starts by illuminating the tissue under study using light having at least the wavelengths of approximately 680 nm, 720 nm, 760 nm and 890 nm. Light that has passed through a portion of the tissue is then sensed at a predetermined distance from the source of the illumination. A value of attenuation of light at each of wavelengths of illumination of the tissue is then determined. A second derivative value of the light attenuation at 720 nm is calculated using the equation (Second Derivative Attenuation)$_{720}$=Attenuation$_{760}$−2(Attenuation$_{720}$)+Attenuation$_{680}$. A second derivative value of the light attenuation at 760 nm is calculated through the equation (Second Derivative Attenuation)$_{760}$=Attenuation$_{890}$−2(Attenuation$_{760}$)+Attenuation$_{720}$. Next, a scaled (Second Derivative Attenuation)$_{720}$ is determined as a function of the (Second Derivative Attenuation)$_{720}$ divided by the (Second Derivative Attenuation)$_{760}$. Lastly, the scaled (Second Derivative Attenuation)$_{720}$ is compared to stored data relating hemoglobin oxygenation to the scaled (Second Derivative Attenuation)$_{720}$ to determine a hemoglobin oxygenation percentage.

In yet still another method for determining the level of hemoglobin oxygenation in tissue with at least one confounding chromophore present in the tissue under study, the process begins with the illuminating of the tissue under study using light at wavelengths such that a scaled 2nd derivative attenuation measurement for the confounding chromophore is substantially similar to a scaled 2nd derivative attenuation measurement for hemoglobin. Next, light that has passed through a portion of the tissue is sensed at a predetermined distance from the source of the illumination. A light attenuation value at each of wavelength of tissue illumination is then determined. A second derivative value of the light attenuation at 720 nm is then determined. A second derivative value of the light attenuation at 760 nm is calculated. A scaled (Second Derivative Attenuation)$_{720}$ is determined as a function of the (Second Derivative Attenuation)$_{720}$ divided by the (Second Derivative Attenuation)$_{760}$. Lastly, the scaled (Second Derivative Attenuation)$_{720}$ is compared to stored data relating hemoglobin oxygenation to the scaled (Second Derivative Attenuation)$_{720}$ to produce a hemoglobin oxygenation percentage.

In still another method for determining the level of a selected chromophore in tissue with at least one confounding chromophore present in the tissue under study, the process begins with the illuminating of tissue under study using light at wavelengths such that scaled 2nd derivative attenuation measurement for the confounding chromophore is substantially similar to the scaled 2nd derivative attenuation measurement for the selected chromophore (analyte). Light that has passed through a portion of the tissue is then sensed at a predetermined distance from the source of the illumination. A value is then determined that is representative of the attenuation of light at each of wavelengths of illumination of the tissue. A value is also determined representative of the second derivative value of the light attenuation at the first wavelength A separate value is also determined that is representative of the second derivative value of the light attenuation at the second wavelength. A scaled Second Derivative Attenuation at the first wavelength is then determined as a function of the Second Derivative Attenuation at the first wavelength divided by the Second Derivative Attenuation at the second wavelength. Lastly, the scaled Second Derivative Attenuation value is compared to stored data relating hemoglobin oxygenation to the scaled Second Derivative Attenuation at the first wavelength to produce a hemoglobin oxygenation percentage. Additionally, the light may be structured so that there is at least a first wavelength at which the second derivative attenuation for the selected chromophore is near a local minimum and a second wavelength at which the second derivative attenuation for the selected chromophore is near a local maximum.

One embodiment of a system according to the present invention is a measurement system for determining a relative concentration of a first form of a chromophore in a tissue sample. The chromophore may be present in tissue under study in at least first and second forms. Confounding chromophores may also be present. The system includes means for irradiating a tissue sample with light at wavelengths such that scaled 2nd derivative attenuation measurement for the confounding chromophore is substantially similar to the scaled 2nd derivative attenuation measurement for the selected chromophore, means for detecting the spectral data emitted from said tissue, means for determining a first 2d derivative spectrum value of the spectral data at a first wavelength within said wavelength range at which the first 2d derivative spectrum value varies with the concentration of the first form of the chromophore, means for determining a second 2d derivative spectrum value of the spectral data at a second wavelength within said wavelength range at which the second 2d derivative spectrum value varies with the concentration of at least a second form the chromophore, means for deriving a scaled, 2d derivative spectrum value from information comprising the first and second 2d derivative spectrum values, means for storing a correlation which provides the relative chromophore concentration as a function of the scaled, 2d derivative spectrum value, and means for determining the relative concentration of the first form of the chromophore in the tissue sample from information comprising the scaled, 2d derivative spectrum value and the correlation. The system may include a computer with memory. Additionally, the light may be structured so that there is at least a first wavelength at which the second derivative attenuation for the selected chromophore is near a local minimum and a second wavelength at which the second derivative attenuation for the selected chromophore is near a local maximum.

In another embodiment, the invention is a measurement system for determining a relative concentration of a first form of a chromophore in a tissue sample. The chromophore may be present in tissue under study in at least first and second forms. Confounding chromophores may also be present. The system includes a memory for storing data representative of a correlation which provides the relative concentration of the first form of the chromophore as a function of a scaled, 2d derivative spectrum value input, wherein the scaled second derivative value input is derived from a spectral response obtained from the tissue sample using light at wavelengths such that scaled 2nd derivative attenuation measurement for the confounding chromophore is substantially similar to the scaled 2nd derivative attenuation measurement for the selected chromophore, a light source assembly for generating spectroscopic radiation for irradiating the tissue sample, a spectroscopic detector for detecting the spectral response emitted by the tissue sample responsive to irradiation with the spectroscopic radiation and a control system interfaced with the memory and the spectroscopic detector such that the control system generates the scaled, second derivative spectrum value of the tissue sample from information comprising the spectral response of the tissue sample and the control system generates information representative of the relative concentration of the first form of the chromophore in the tissue sample from information comprising the scaled, second derivative spectrum value and the correlation provided in the memory. Additionally, the light may be structured so that there is at least a first wavelength at which the second derivative attenuation for the selected chromophore is near a local minimum and a second wavelength at which the second derivative attenuation for the selected chromophore is near a local maximum.

Table 1 shows predicted error in StO2 measurements for different confounding chromophore attenuation conditions.

Table II. The Lambert-Beer equation was used to create 2nd derivative absorbance ratios at variable % $SO_2$, Hbt and pathlength. Unlike the 2nd derivative values at 720 nm and 760 nm, the scaled 2nd derivative attenuation (Eq. 7) varies with % $SO_2$ only and does not change with Hbt and pathlength. The model results are applicable to a non-scattering environment where $HbO_2$ and HHb are the principal absorbers.

DETAILED DESCRIPTION OF THE INVENTION

Figure 9:
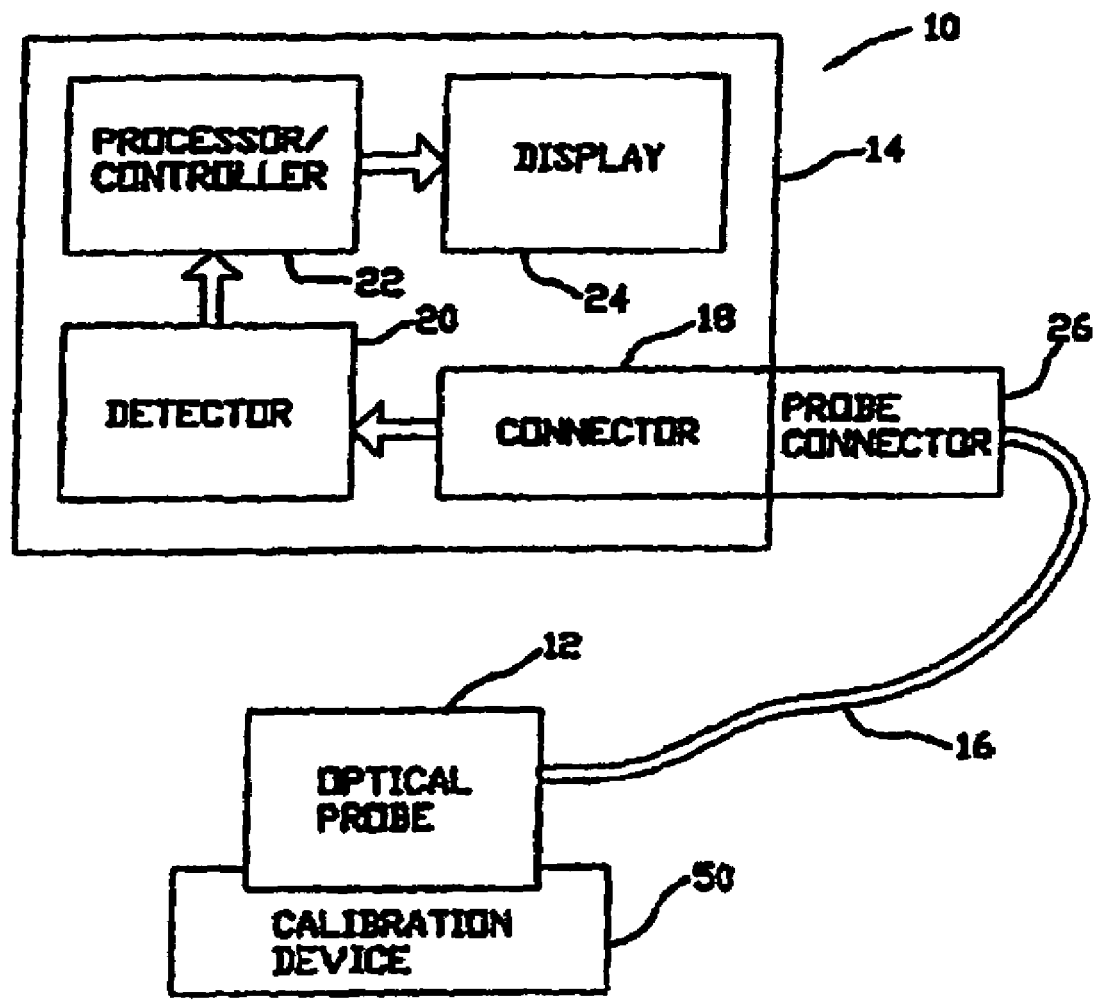
FIG. 9 is a block diagram of a blood spectroscopy device.
Figure 10:
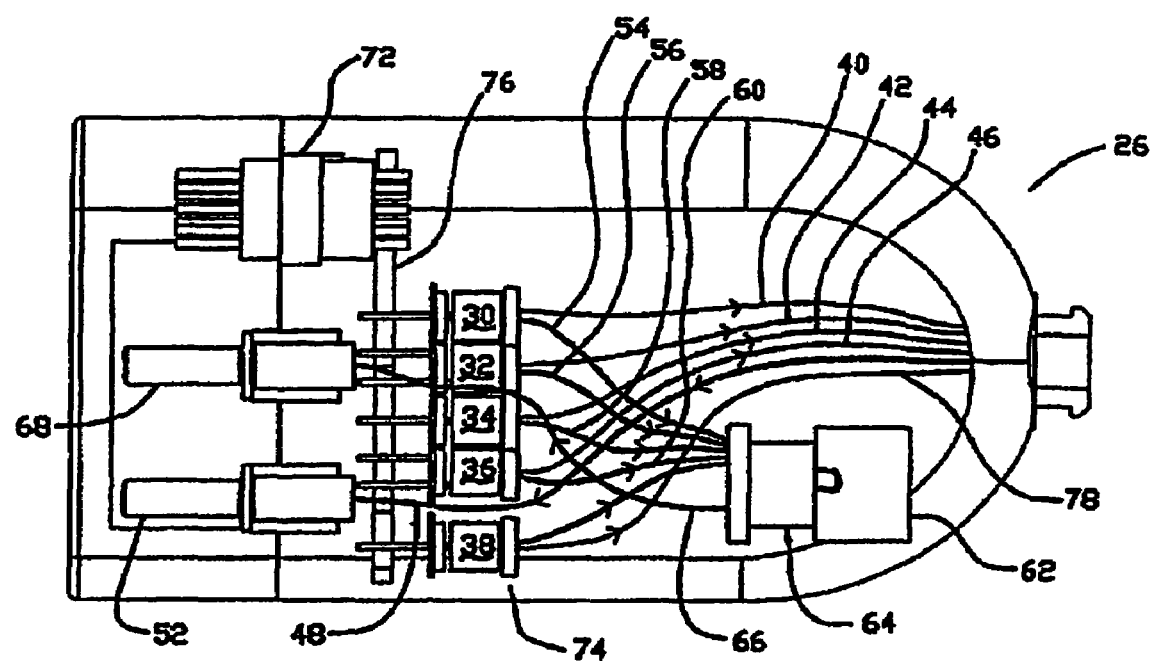
FIG. 10 is an elevation view of light sources in a spectroscopy system.

Referring now to FIGS. 9 and 10, thereshown are a basic structure for a spectrometer 10. The spectrometer can include an optical probe 12 and a base unit 14. The optical probe can include light sources or light pathways for placing light on tissue under study and collecting light from the tissue under study. The light pathways can be carried in cable 16. A probe connector 26 connects the optical probe to the base unit 14. Base unit 14 includes a connector 18, a detector 20, a processor/controller 22 and a display 24. The connector 18 is for connecting the base unit to the optical connector. Detector 20 measures light collected from the tissue at specific wavelength ranges and produces one or more output signals that are proportional to the sensed light. The processor controller then uses the equations noted above to calculate a final value for $StO_2$ from the output signal(s). The display 24 receives and displays the $StO_2$ value. Calibration device 50 can be a synthetic target that consistently simulates light reflection and scattering in tissue for calibration use.

FIG. 10 shows one possible location of the LEDs used in a spectrometer. In the present embodiment, probe connector 26 carries LEDs 30, 32, 34, 36. LED 38 can be included and used to signal when a calibration event is to occur. Fibers 40, 42, 44, and 46 are used to carry light to the tissue. Fiber 48 is used to carry light back from the tissue to the detector via connector 52. Fibers 54, 56, 58 and 60 are used to carry the LED light to a light mixer and back to the detector (via fiber 66 and connector 68) for measurement of the light sources prior to passing through the tissue under study. The probe connector 26 also preferably has a 14 pin electrical connector 72 and an optical fiber fixturing ferrule 74 for each of the LED's 30, 32, 34, 36, and 38, each of which are mounted in a PC board 76, along with connector 72. It is to be understood that the arrows on fibers 40, 42, 44, 46 are to indicate "to probe tip" while the arrows on fiber 48 are to indicate "from probe tip."

The wavelength gap interval (described $StO_2$ Algorithm below) is chosen so that tissue numerator and denominator 2nd derivative attenuation measurements are affected in a nearly equal manner. The resultant 2nd derivative attenuation bias resembles a common gain factor among the two attenuation measurements. Ratioing the two 2nd derivative measurements effectively removes the common bias and provides an analyte measurement that is robust to the presence of the non-desired chromophore (i.e. water).

$StO_2$ Algorithm

Tissue attenuation (A) measurements were calculated as—log (sample intensity/reference intensity) for each measured wavelength. At a fixed wavelength gap interval (gap), the second derivative of attenuation (2D) is obtained at each wavelength ($\lambda$) nm using an algebraic simplification of the difference between two first derivative attenuation (D) measurements calculated at a similar gap interval:

$$D_\lambda = A_\lambda - A_{\lambda-gap} \quad [1]$$

$$D_{\lambda+gap} = A_{\lambda+gap} - A_\lambda \quad [2]$$

$$2D_\lambda = D_{\lambda+gap} - D_\lambda \quad [3]$$

$$2D_\lambda = A_{\lambda+gap} - 2A_\lambda + A_{\lambda-gap} \quad [4]$$

A wavelength gap of 40 nm is used to calculate the 2nd derivative attenuation at two wavelengths, 720 and 760 nm. These two 2nd derivative attenuation signals are related to the four measured attenuation wavelengths as follows:

$$2D_{720} = A_{760} - 2A_{720} + A_{680} \quad [5]$$

$$2D_{760} = A_{800} - 2A_{760} + A_{720} \quad [6]$$

For each tissue spectrum measurement a scaled $2D_{720}$ value is used to predict tissue % $StO_2$ from a predetermined empirical calibration relationship:

$$\text{scaled } 2D_{720} = 2D_{720}/2D_{760} \quad [7]$$

% $StO_2$ Algorithm and Calibration Method

A plot of published pure component $HbO_2$ and Hb absorption spectra and 2nd derivative absorption transformations using both narrow (1 nm) and wide (40 nm) wavelength gaps (FIG. 6) reveals the reasons for choosing an algorithm incorporating a 40 nm gap 2nd derivative transformation. The absorbance profile of $HbO_2$ (FIG. 6A) is non-linear within the 680 to 760 nm wavelength region. With a wide 40 nm gap, the $HbO_2$ 2nd derivative at 720 nm is approaching maximal amplitude (FIG. 6D) while the corresponding 1 nm gap amplitude (FIG. 6B) is effectively zero. A larger 40 nm gap $HbO_2$ spectral contribution allows a more precise estimate of % $SO_2$. The 760 nm Hb specific 40 nm gap 2nd derivative amplitude (FIG. 6D), being larger than the corresponding 1 nm gap amplitude (FIG. 6B), also provides a robustness to noise. The 1 nm gap spectra required curve fitting of the absorption spectra to provide visually presentable 2nd derivative spectra while the 40 nm gap 2nd derivative spectra required no absorption smoothing.

Figure 7:
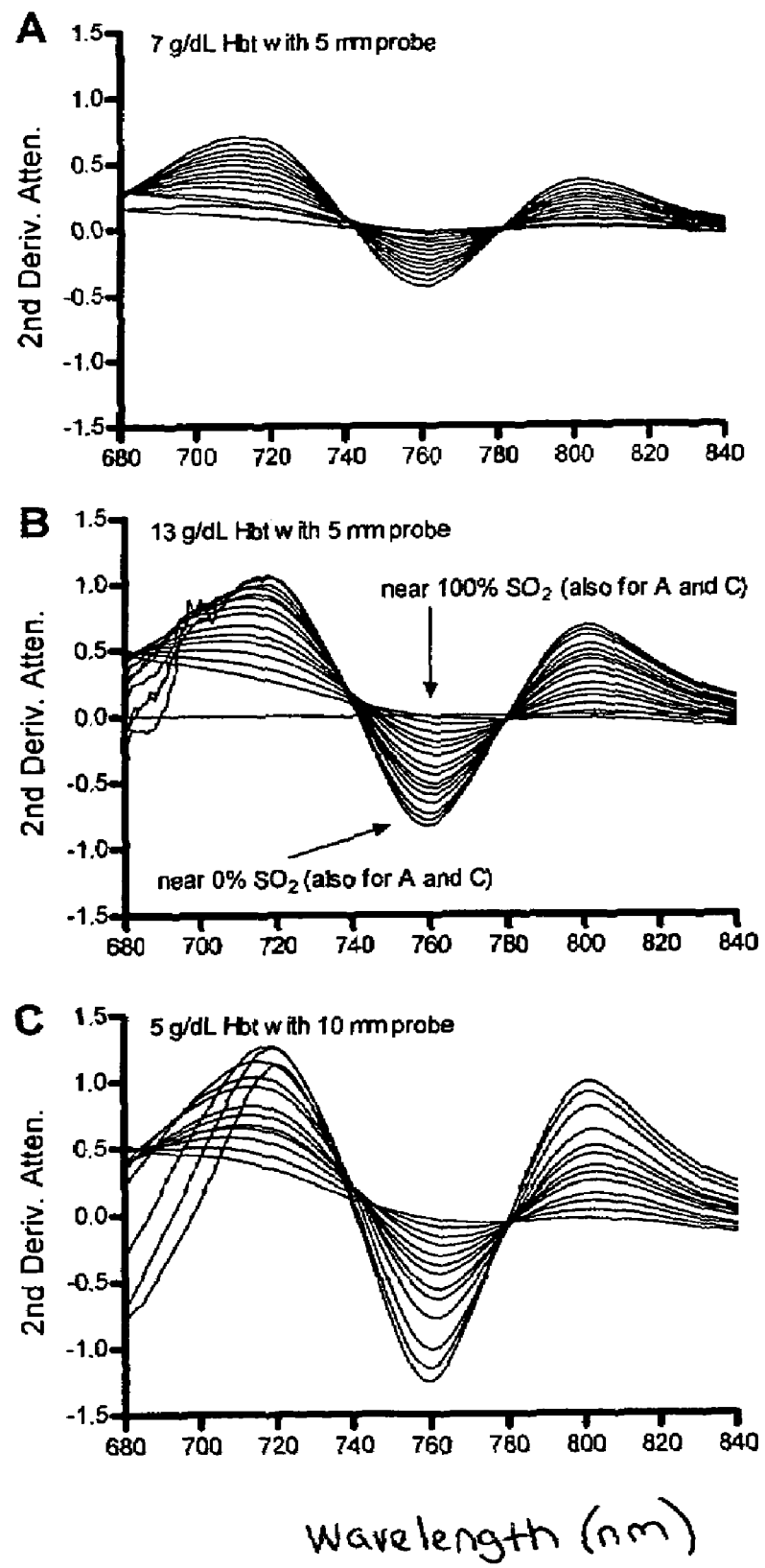
FIGS. 7A-C are graphs of second derivative attenuation vs. wavelength for bovine blood have different concentrations of hemoglobin and using different probe spacings.

Although 2nd derivative processing of attenuation spectra minimizes the effects of wavelength dependent scattering (tilt) and lack of photometric calibration (offset) from attenuation spectra, an optical pathlength (probe spacing) component shows up as a gain factor within 2nd derivative blood spectra (FIG. 7). The ratio of two 2nd derivative attenuation measurements was the premise for providing a % $SO_2$ specific measurement that would be inherently robust to optical pathlength and Hbt [see Table II].

Figure 6:
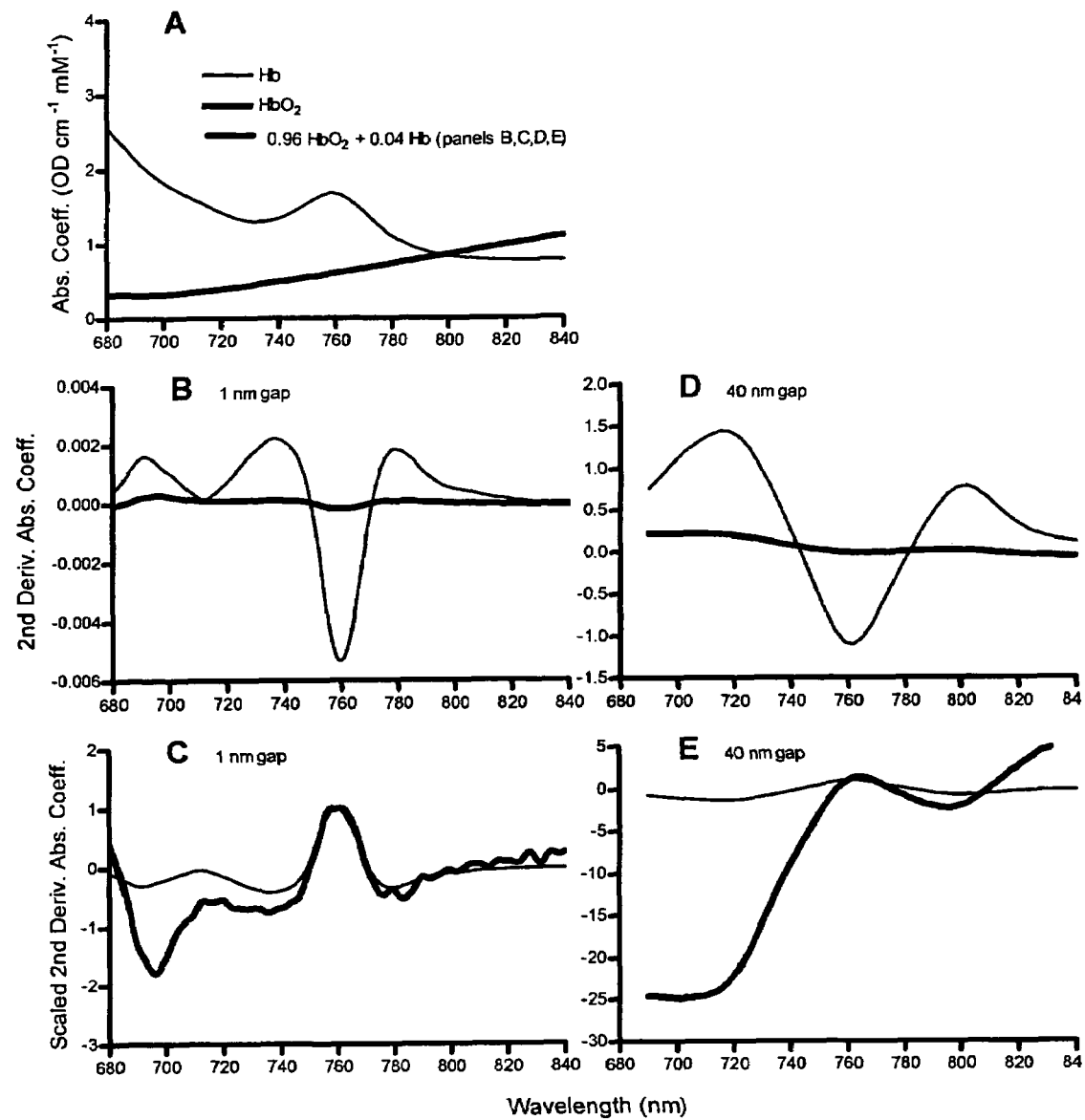
FIG. 6A is a graph of absorption vs. wavelength for deoxyhemoglobin (Hb) and oxyhemoglobin ($HbO_2$).
FIG. 6B is a graph of second derivative of absorbance vs. wavelength for Hb and $HbO_2$ with a 1 nm gap.
FIG. 6D is a graph of second derivative of absorbance vs. wavelength for Hb and $HbO_2$ with a 40 nm gap.
FIG. 6C is a graph of the scaled second derivative of absorbance vs. wavelength for Hb and $HbO_2$ with a 1 nm gap.
FIG. 6E is a graph of the scaled second derivative of absorbance vs. wavelength for Hb and $HbO_2$ with a 40 nm gap.

The 760 nm 2nd derivative attenuation is ideally suited for this method because the wide gap wavelength region (720 nm to 800 nm for 40 nm gap) has no spectral contribution from $HbO_2$ and exhibits maximal amplitude change with variable % $SO_2$, at fixed Hbt and pathlength. With a prerequisite 760 nm 2nd derivative wavelength, the 720 nm 2nd derivative wavelength was chosen for its relatively close proximity to 760 nm and its sensitivity to both $HbO_2$ and Hb. Since the 40 nm gap interval equals the distance between the numerator and denominator 2nd derivative wavelengths, a reduction from six to four measurement wavelengths occurs (Eqs. 5 and 6). Although a similar reduction of wavelengths would result from using an 800 nm 2nd derivative measurement relative to 760 nm, the 720 nm scaled point is chosen because of its larger and more varied 2nd derivative amplitude with respect % $SO_2$ (FIG. 6 panels C,E).

There are several approaches that could have been used to develop the calibration curves relating the scaled $2D_{720}$ measurements (Eq. 7) to hemoglobin oxygen saturation in tissue. Since there is currently no measurement standard for measuring tissue hemoglobin oxygen saturation, an in vivo approach would involve some assumption regarding how the NIRS signal best represented a balance between invasively measured arterial and venous % $SO_2$ near the measured tissue site.

Figure 8:
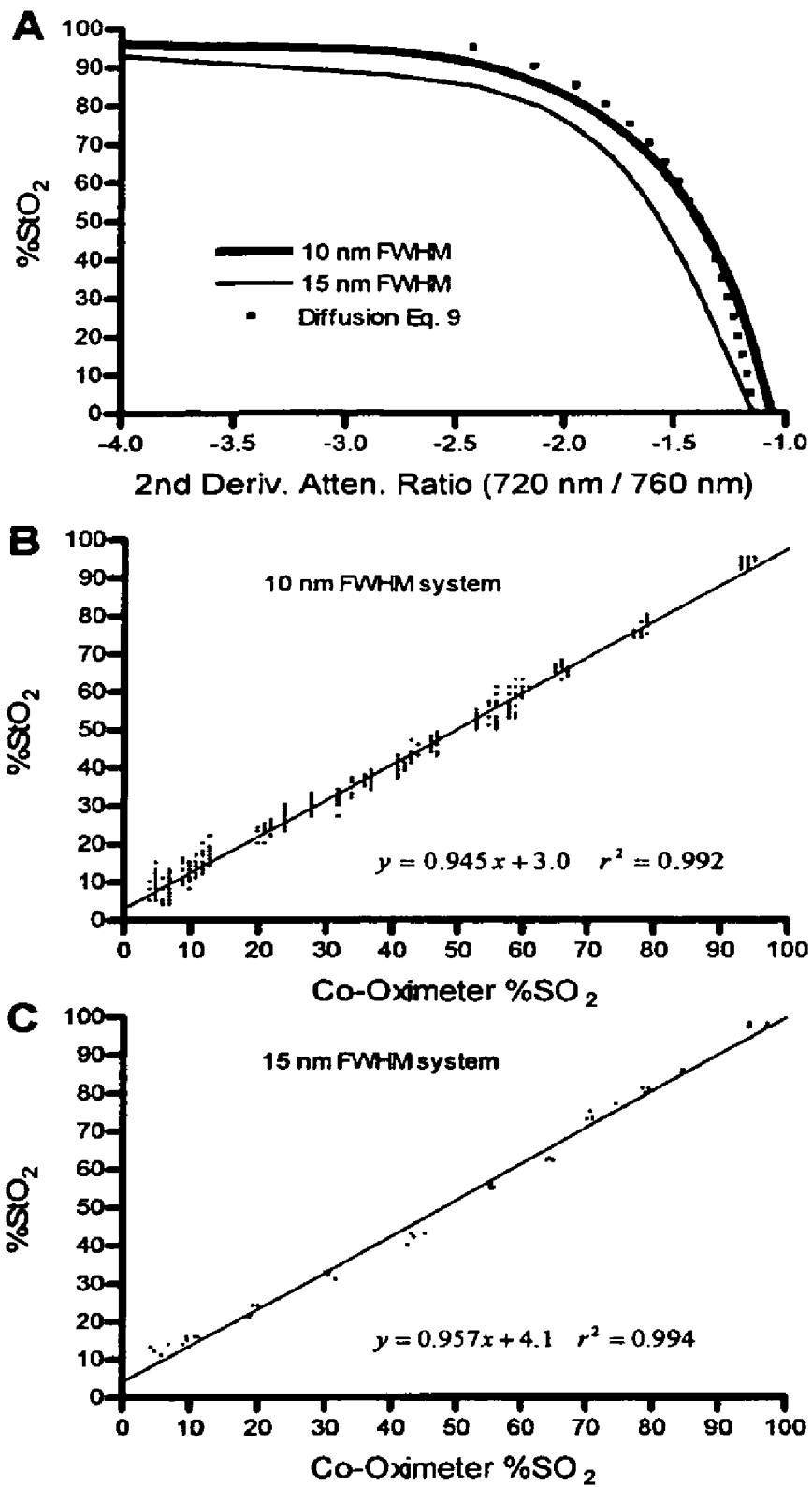
FIG. 8A is a graph of $StO_2$ percentages vs. second derivative attenuation ratios for different spectrometers.
FIGS. 8B-C are graphs of the correlation between the different spectrometers and a reference co-oximeter percent $SO_2$ measurement.

A mathematical model approach to calibration could involve a diffusion theory equation combined with measured $\mu_a$ of the significant tissue absorbers and $\mu'_s$ for the desired tissue bed. The single layer diffusion theory equation (Eq. 8) (see below) provided a calibration relationship using published absorption data that was not too dissimilar from the in vitro developed calibration curves (FIG. 8A). To minimize measurement bias, the absorption coefficient data should be empirically measured with the same optical equipment used for measuring % $StO_2$ to account for how center wavelength and bandwidth resolution influences a calibration curve.

An in vitro calibration method was chosen because it provided a controlled test environment for characterizing repeatability of $StO_2$ measurements among the multiple spectrometer designs manufactured (see FIGS. 8B-C). One in vitro method reviewed involved immersing a 5 mm probe in diluted whole blood, 5 to 12 g/dL, having sufficient volume to contain nearly all optical pathlengths. This method was used to demonstrate the variability of 2nd derivative amplitudes versus % $SO_2$, Hbt and probe spacing (FIG. 7) but was not used to develop the depicted calibration curves (FIG. 8A) because the test environment provided too much attenuation of signal with probes greater than 10 mm spacing. Although dilution of hemoglobin significantly below 5 g/dL would reduce absorption and allow long pathlength measurements, the blood scattering properties would be significantly reduced as the red blood cell count decreases.

Intralipid emulsion solution has been used to provide a constant scattering environment in which to dilute Hbt to assumed tissue levels, 1 or less g/dL. Unfortunately blood co-oximeters are the current standard for blood % $SO_2$ and have limited accuracy below 5 g/dL Hbt even before considering the possible interference from Intralipid. The authors have noted some discrepancies between % $SO_2$ measured with an IL482 co-oximeter and % $SO_2c$ calculated with an IL blood Gas analyzer (% $SO_2c$ generally 10 units higher across full range with whole bovine blood). Because of this discrepancy it was uncertain whether Hill type equations for predicting % $SO_2$ from pH, $pO_2$ and temperature could be accurately extrapolated to all possible % $SO_2$ values at hemoglobin concentrations well below the normal physiologic range of blood.

A two layer model for manipulating a thickness of blood above a constant scattering layer, LD45 Plastazote foam, was used to develop the $StO_2$ vs. scaled $2D_{720}$ relationship because blood full range % $SO_2$ could be accurately defined with a co-oximeter and the possible confounding effects of carboxyhemoglobin and methemoglobin could be investigated. The two layer model additionally allowed all probe spacings of this study to be correlated to co-oximeter % $SO_2$.

The tissue Model Input (FIGS. 3A, 3C, 4B, 5C) used a single layer infinite slab diffusion theory equation to create computer simulated tissue attenuation (A) spectra at variable inputs of tissue absorption coefficient ($\mu_a$), scattering coefficient ($\mu'_s$) and probe spacing ($\rho$). This Model Input has been previously used to evaluate NIRS algorithm performance and has the form:

$$A = -\log 10\left(\frac{\sinh(\sigma/\mu'_s)}{\sinh(\sigma_p) \times (2\pi)^{0.5}}\right) \text{ whereas } \sigma = \sqrt{3\mu_a(\mu_a + \mu'_s)} \quad [8]$$

For this single layer tissue model the tissue absorbance coefficient ($\mu_a$) was estimated from absorbers thought to have the most significant spectral contribution for the % $StO_2$ algorithm wavelength region, 680 to 800 nm. Within this region water has a non-linear spectral contribution that is amplified due to its high concentration in tissue, 70 wt % or 43 M considering lean tissue density of 1.1 Kg/L. Although fat has a lipid specific absorption peak near 930 nm, it is assumed to have an effect similar to water considering adipose tissue comprises 20% water.

Figure 1A:
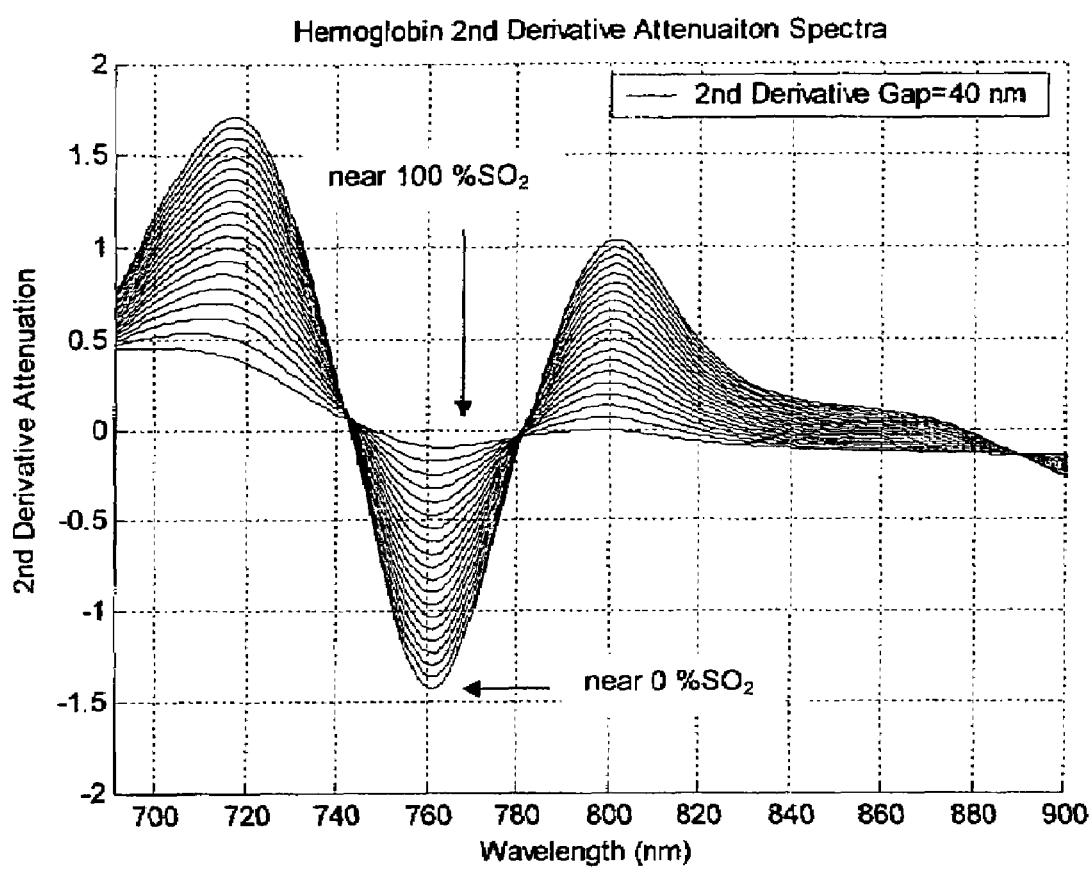
FIG. 1A is a graph of $2^{nd}$ derivative hemoglobin attenuation spectra with a wavelength gap of 40 nm.
Figure 1B:
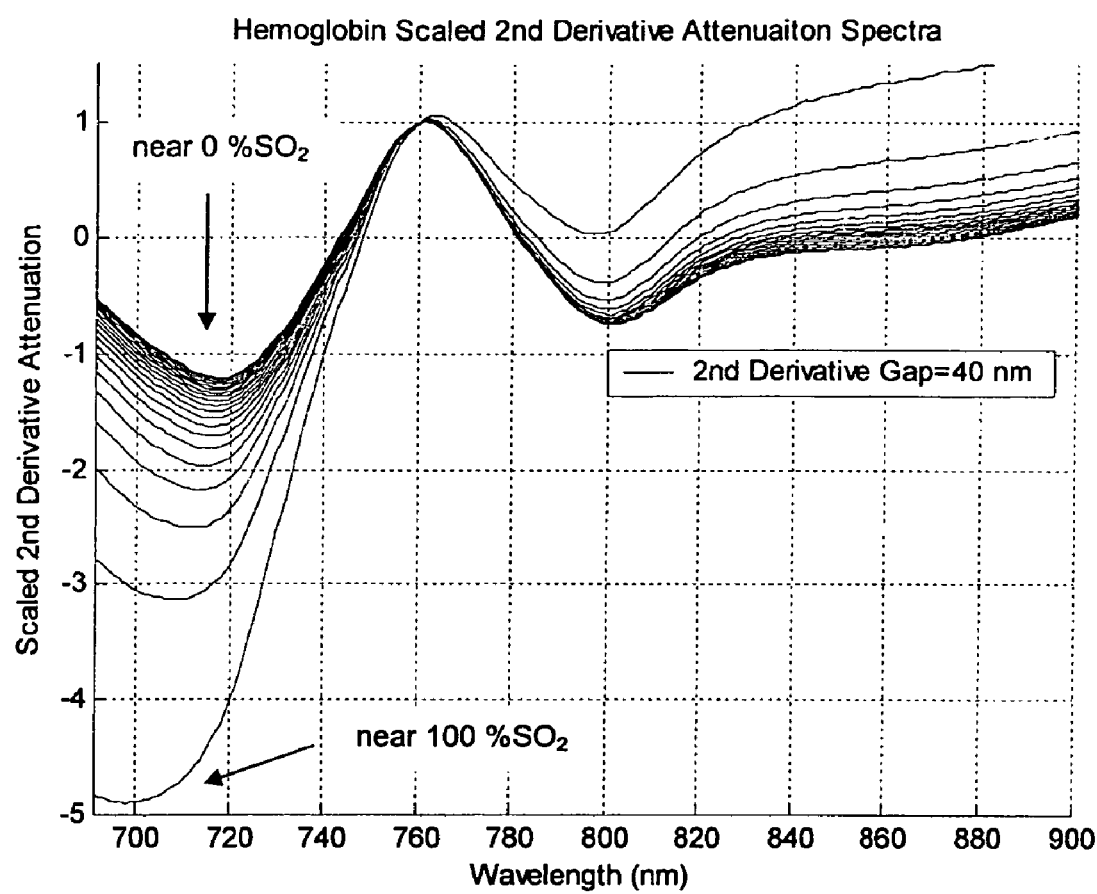
FIG. 1B is a scaled version of the graph of FIG. 1A.

Consider a case where the gap interval used to calculate a 2nd derivative attenuation is fixed at 40 nm for both a numerator (720 nm) and denominator (760 nm) 2nd derivative attenuation measurement (equations 5 and 6). FIG. 1B shows the ratioed and FIG. 1A shows the non-ratioed 2nd derivative spectral features for variable hemoglobin oxygen saturation at a fixed level of total hemoglobin (Hbt) concentration. A calibration curve relating the ratioed (scaled) 720 nm 2nd derivative attenuation to % $StO_2$ is represented in FIG. 8A. The hardware used to attain the 10 nm FWHM input to create the curve represented in FIG. 8A is as follows. A commercially available spectrometer, InSpectra™ Tissue Spectrometer Model 325 (Hutchinson Technology Inc, Hutchinson, Minn.), includes of four simultaneous operated photomultiplier tubes coupled to interference filters having center wavelengths of 680, 720, 760 and 800 nm. All filters have a bandwidth of 10 nm FWHM. A single 400 micron glass optical fiber coupled sampled light to a series of dichroic mirrors to direct light segments to the appropriate wavelength detector. Four center wavelength matched light emitting diodes (LED) having bandwidths 3-4 times the detection bandwidth are coupled to 3 meter length 400 micron optical fibers. All four send fibers are coupled to a 1000 micron 300 mm length plastic optical fiber to adequately mix the discrete light wavelengths prior to being launched into the measurement sample. Probe spacings of 12 mm, 15 mm, 20 mm and 25 mm were used. A portion of the LED light is directly coupled to the receive optics in order to correct for light source and detector drift. LED signals are modulated, near 100% depth at 760 Hz, and synchronously detected to exclude ambient light and dark signals. Sample measurement signals are updated every 3.5 seconds prior to smoothing with a 5 point running average.

Table 1 shows the exaggerated effects of an interfering chromophore for the following assumed % $StO_2$ conditions: $2D_{720}=0.15$ (Eq. 5), $2D_{760}=-0.10$ (Eq. 6) and scaled $2D_{720}=-1.5$ (Eq. 7). The Table 1 results show that a chromophore exhibiting 2nd derivative attenuation (columns B and D) in example rows 4 and 5 does not significantly alter the combined ratioed 2nd derivative attenuation (column F) nor the $StO_2$ error (column H). For this example the chromophore bias for the numerator and denominator were of opposite sign and shifted both the numerator and denominator 2nd derivative attenuations either closer to zero or further from zero. The ratio of the interfering chromophore bias (column B divided by column D, not shown) is more similar to the ratio (column F) of the analyte chromophore (example row 1).

For the case of water, being the interfering chromophore for the analyte measurement of % $StO_2$, the wavelength gap interval used to calculate a 2nd derivative attenuation measurement can be purposefully selected to reduce the $StO_2$ measurement error in tissue. There are several ways in which the gap interval may be chosen without sacrificing the inherent sensitivity of a scaled $2D_{720}$ measurement (Eq. 7) to tissue hemoglobin oxygen saturation.

A gap interval of 28 nm common to both the 720 and 760 nm 2nd derivative attenuation measurements is one option for mitigating measurement error due to water. Equations 5, 6 and 7 then become:

$$2D'_{720}=A_{748}-2A_{720}+A_{692} \quad [5']$$

$$2D'_{760}=A_{788}-2A_{760}+A_{732} \quad [6']$$

$$\text{scaled } 2D'_{720}=2D'_{720}/2D'_{760} \quad [7']$$

Figure 2A:
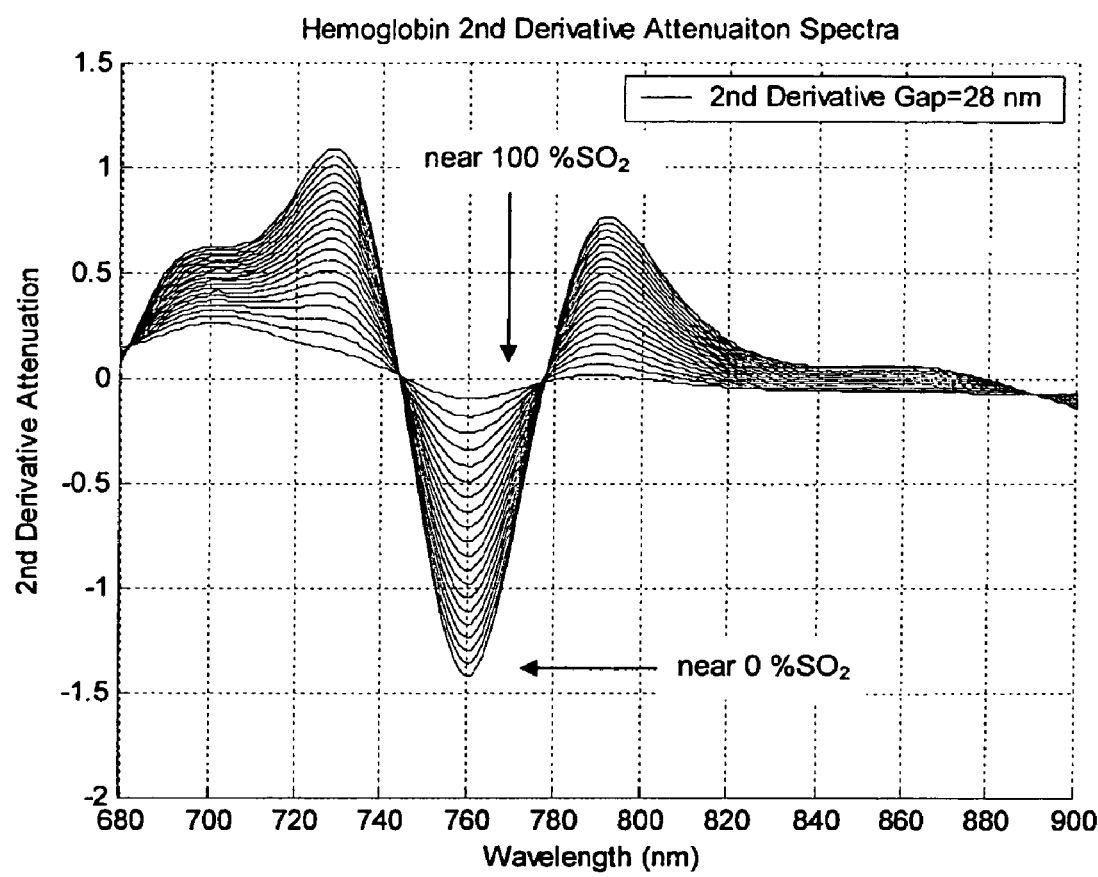
FIG. 2A is a graph of $2^{nd}$ derivative hemoglobin attenuation spectra with a wavelength gap of 28 nm.
Figure 2B:
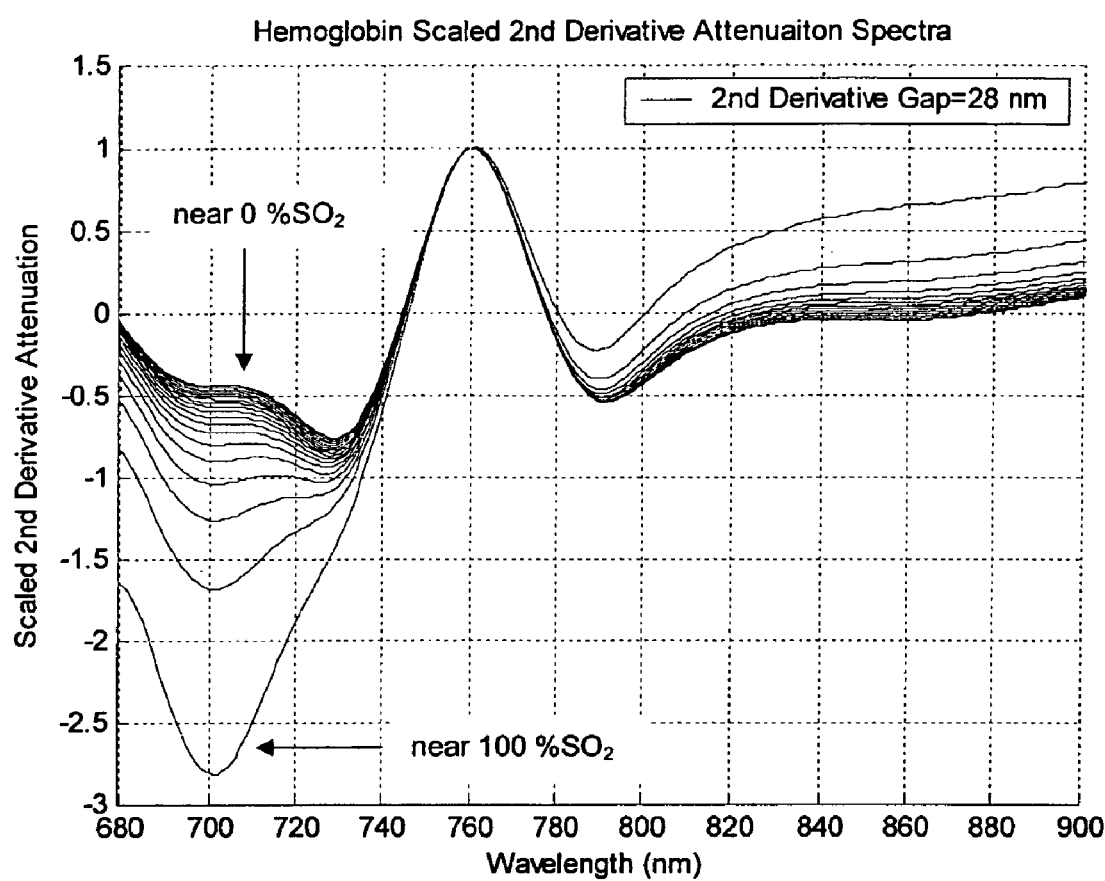
FIG. 2B is a scaled version of the graph of FIG. 2A.
Figure 3:
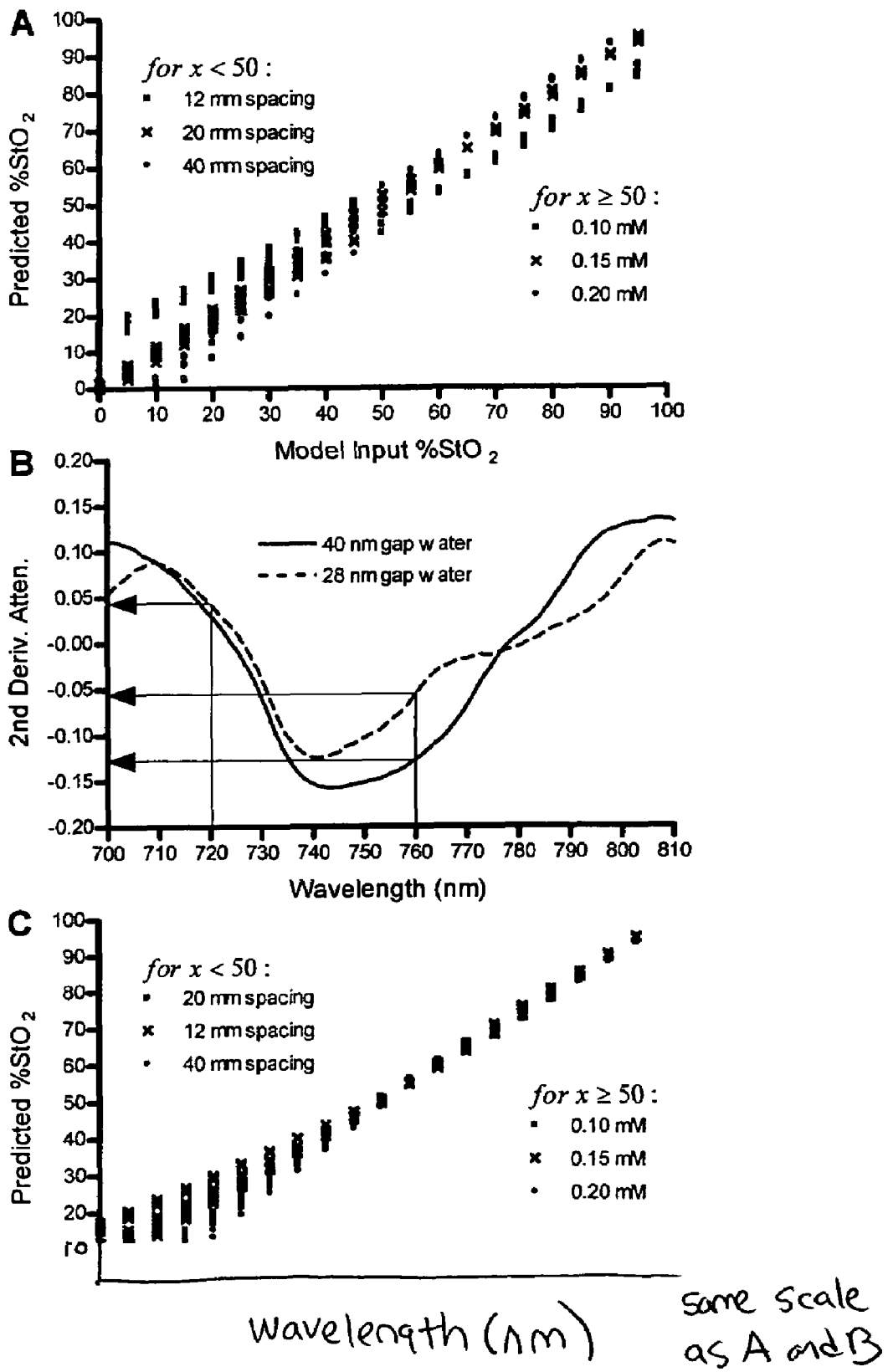
FIG. 3A is a graph of predicted % $StO_2$ vs. Model Input StO2 having common 40 nm gap wavelength spacings.
FIG. 3B is a graph of second derivative attenuations of a light passing through water vs. wavelength with different wavelength spacings.
FIG. 3C is a graph of predicted $StO_2$ vs. Model Input $StO_2$ having common 28 nm gap wavelength spacings.

FIG. 2 describes 28 nm gap hemoglobin 2nd derivative spectra at variable % $StO_2$ and fixed total hemoglobin concentration. For a common 40 nm gap interval, FIG. 3A shows how % $StO_2$ measurements above 50% change with total hemoglobin concentration (as modeled using diffusion equation 8). This Hbt cross talk effect is primarily due to the spectral contribution of water which becomes a more significant proportion of total tissue absorption has hemoglobin absorption is reduced. At 70% tissue concentration, the water peak alone resembles a small deoxyhemoglobin signal (FIG. 3B). An additional model analysis, using an $StO_2$ algorithm having a common gap interval of 28 nm for the 720 nm and 760 nm 2nd derivative attenuation measurements, indicates that a 28 nm gap $StO_2$ algorithm would be more robust to the spectral influence of water (FIG. 3C). For 28 nm gap 2nd derivative tissue water attenuation, the 720 nm and 760 nm derivatives have a more similar amplitude of opposite sign (FIG. 3B) which mitigates the spectral contribution of water on the scaled 720 nm 2nd derivative attenuation. Although this 28 nm gap method reduces water induced % $StO_2$ errors, 6 measurement wavelengths would be required since the numerator and denominator 2nd derivative attenuation wavelengths (Eq. 5' and 6') no longer share common wavelengths. Also, the smaller wavelength gap of 28 nm reduces 720 nm 2nd derivative attenuation sensitivity to $HbO_2$ and would produce an algorithm which is more sensitive to spectrometer noise.

Figure 4A:
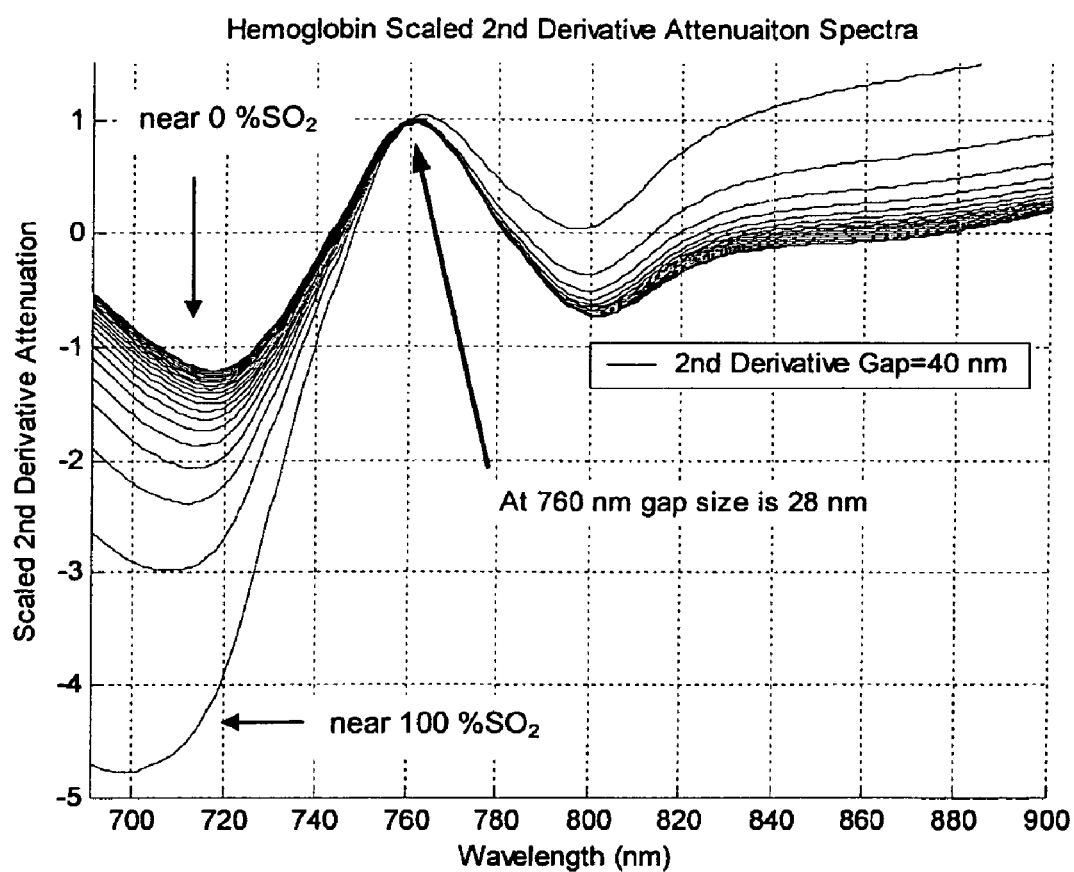
FIG. 4A is a graph of a scaled second derivative attenuation vs. wavelength with different wavelength gaps in the numerator and denominator of the scaling operation.
Figure 4B:
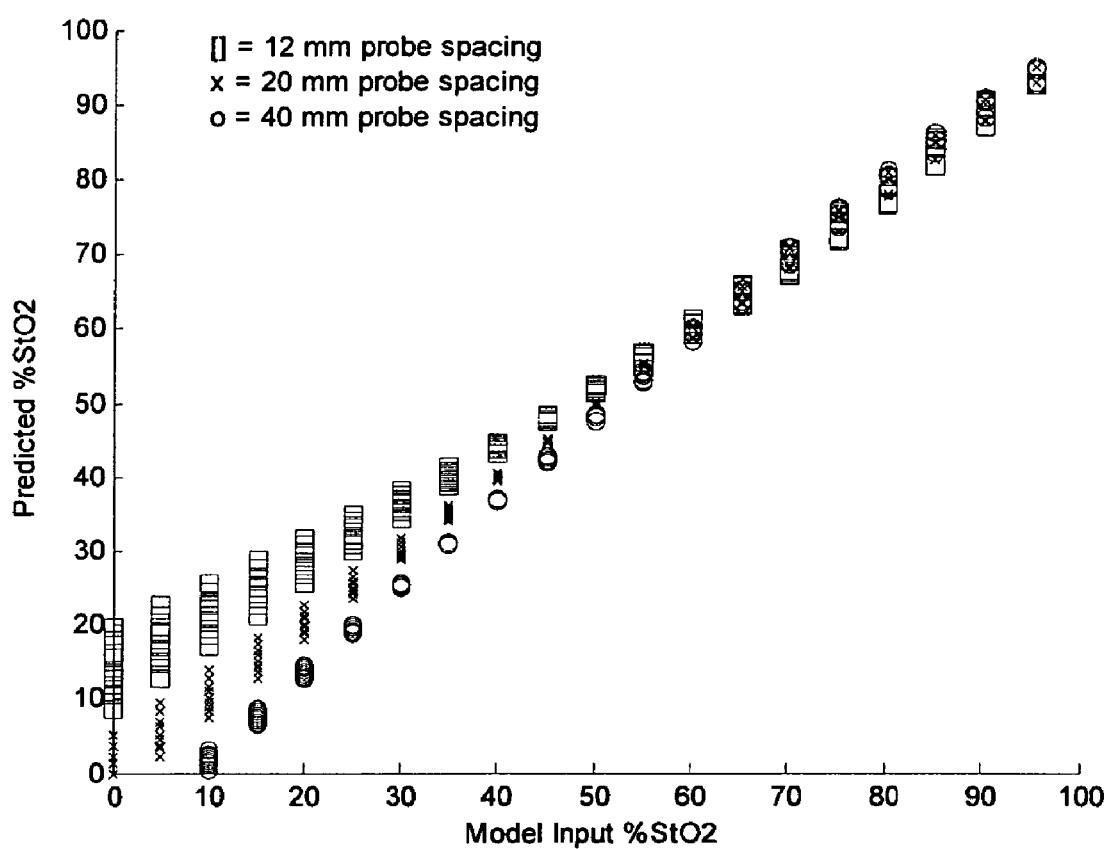
FIG. 4B is a graph of predicted % $StO_2$ vs. Model Input $StO_2$ with different wavelength gaps in the numerator and denominator of the scaling operation.

A comparison of FIGS. 1A and 2A show that the 40 nm gap spectra (FIG. 1A) provides more 720 nm dynamic range (sensitivity) to % $StO_2$ than the corresponding 28 nm gap spectra (FIG. 2A). At 760 nm, both the 40 nm gap and 28 nm gap spectra exhibit similar sensitivity to % $StO_2$. FIG. 3B shows that water has a similar 720 nm 2nd derivative attenuation regardless of wavelength gap (40 nm and 28 nm). At a 28 nm gap, the 760 nm water 2nd derivative (FIG. 3B) becomes more similar in magnitude (but of opposite sign) to the 40 nm gap 720 nm water 2nd derivative attenuation. This combination of different numerator and denominator gap intervals, 40 nm and 28 nm respectively, provides robustness to high $StO_2$ range water interference as shown in FIG. 4B. This modifies equations 5, 6 and 7 to be:

$$2D''_{720}=A_{760}-2A_{720}+A_{680} \quad [5'']$$

$$2D''_{760}=A_{788}-2A_{760}+A_{732} \quad [6'']$$

$$\text{scaled } 2D''_{720}=2D''_{720}/2D''_{760} \quad [7'']$$

An important result of this gap interval combination (equations 5" and 6") is that a scaled $2D_{720}$ calibration curve using a 720 nm 40 nm gap and a 760 nm 28 nm gap produces a nearly identical calibration curve to FIG. 8A which was generated using 40 nm gap intervals for both the 720 nm numerator and 760 m denominator 2nd derivative attenuation wavelengths. This option reduces water measurement error without sacrificing $StO_2$ precision. This uncommon gap combination method requires 5 measurement wavelengths since the 760 nm denominator 28 nm gap and the 720 nm numerator 40 nm gap share one common wavelength (760 nm).

Another option that requires only four measurement wavelengths includes a 40 nm gap 720 nm 2nd derivative attenuation measurement and a 760 nm 2nd derivative attenuation measurement using a non-uniform (transformed) gap interval using wavelengths spaced 40 nm and 130 nm apart. In this case, equations 5 and 6 become:

$$2D'''_{720}=A_{760}-2A_{720}+A_{680} \quad [5''']$$

$$2D'''_{760}=A_{890}-2A_{760}+A_{720} \quad [6''']$$

Figure 5A:
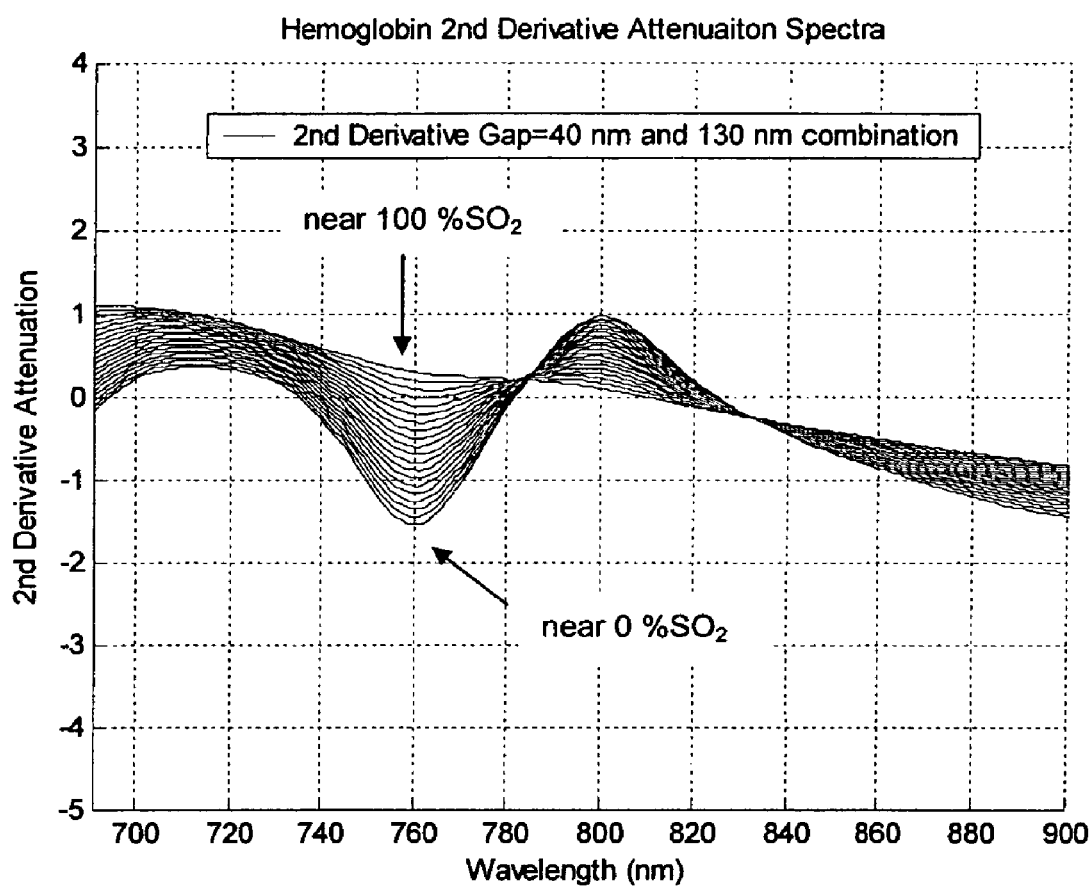
FIG. 5A is a graph of second derivative attenuation vs. wavelength for hemoglobin using a 40 nm/130 nm combination gap across all wavelengths.
Figure 5B:
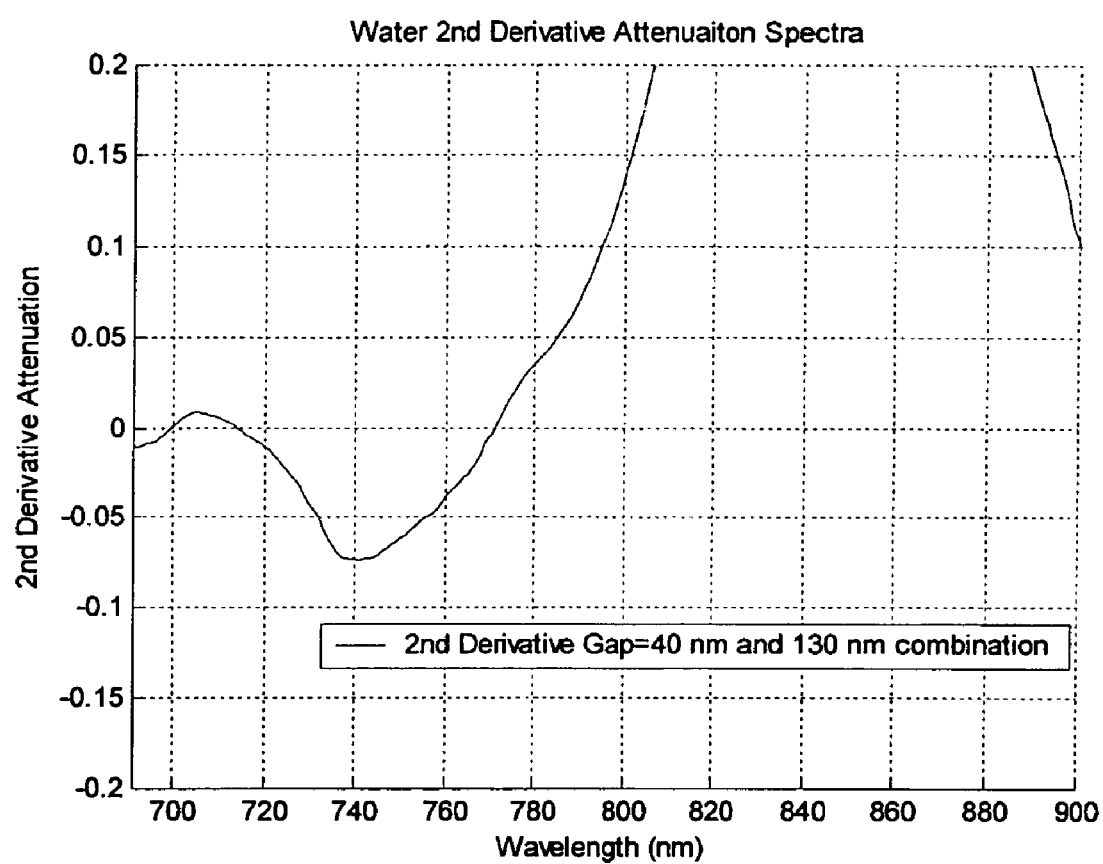
FIG. 5B is a graph of second derivative attenuation vs. wavelength for water using a 40 nm/130 nm combination gap across all wavelengths.
Figure 5C:
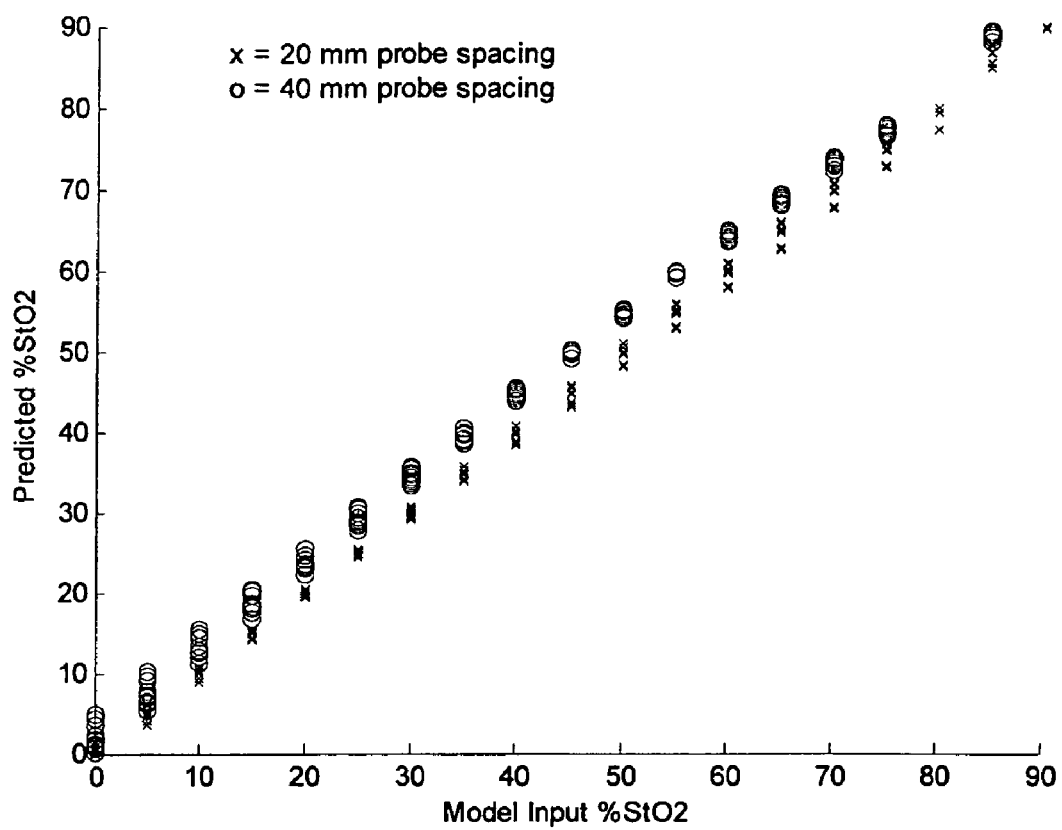
FIG. 5C is a graph of predicted % $StO_2$ vs. Model Input $StO_2$ using a 40 nm/130 nm combination across all wavelengths.

FIG. 5A shows the hemoglobin % $StO_2$ specific spectra using a 40 nm/130 nm combination gap across all wavelengths. FIG. 5B shows how the corresponding 760 nm 2nd derivative attenuation of water (near −0.05) is of opposite sign and of similar magnitude to the 40 nm gap 720 nm 2nd derivative water attenuation, FIG. 3B. Modeled % $StO_2$ results, FIG. 5C show reduced sensitivity to Hbt above 50% $StO_2$ due to the scaled $2D_{720}$ (ratio of equations 5''' and 6''') spectral robustness to water. This leads to equation 7''' being $$\text{scaled } 2D'''_{720} = 2D'''_{720}/2D'''_{760} \quad [7''']$$

Use of these modified equations may require changing the LEDs previously used or disclosed for a spectrometer (for example the 680 nm, 720 nm, 760 nm and 800 nm as identified in U.S. Pat. No. 5,879,294) to wavelengths matching those used in the equations. This means that other wavelengths, such as 692, 732, 748, 788 and 890 nm may also be used. In an alternative embodiment, a continuous wave light source that includes the required wavelengths of light could be filtered at the desired wavelengths to provide light to the tissue. Lasers, for example laser diodes or vertical cavity surface emitting lasers (VCSELS), may also be used.

A scaled (ratioed) 2nd derivative attenuation measurement has a characteristic magnitude that relates directly and significantly to an intended chromophore (analyte) measurement. The nonlinear absorption profile of the analyte (absorbance versus wavelength) is what provides the resultant nonzero 2nd derivative magnitudes for both the numerator and denominator 2nd derivative attenuation measurements used to calculate a scaled 2nd derivative value. A confounding chromophore (also exhibiting significant nonlinear absorption within the measured wavelength region) has a contribution to both the numerator and denominator 2nd derivative attenuation measurements (and resultant scaled 2nd derivative value). This confounding chromophore 2nd derivative contribution reduces the specificity of the measured scaled 2nd derivative attenuation to the desired analyte and therefore creates a measurement error (bias) with regard to the predicted amount of analyte present. This error would change (increase) as the amount of confounding chromophore increased relative to the amount of analyte chromophore.

The disclosed method specifically optimizes the gap interval used to calculate a 2nd derivative attenuation measurement in order to improve specificity of a measured scaled 2nd derivative attenuation measurement to a desired analyte chromophore amount in the presence of a confounding chromophore amount (which would no longer significantly affect the calibration relationship of scaled 2nd derivative attenuation to the desired analyte chromophore).

These wavelengths (from equations 5', 5'', 5''', 6',6'', 6''') are chosen because the spectral features of water do not significantly affect the scaled 2d derivative hemoglobin measurements. The 2nd derivative ratio (the various forms of Eq. 7) of pure water (tissue without hemoglobin) better resembles the 2nd derivative ratio of hemoglobin within the 50-95% oxygen saturation range. For instance, if at 50% StO2 the 2nd derivative ratio of tissue attenuation is −1.5, a gap optimization that gives a similar −1.5 2nd derivative attenuation ratio for pure water will produce an % StO2 measurement that is robust to water. As the water attenuation increases due to concentration and/or probe spacing (pathlength), the pure water second derivative attenuation ratio will remain substantially constant.

The wavelength gap interval, for calculating a numerator and denominator 2nd derivative attenuation measurement, is chosen so that scaled 2nd derivative attenuation measurement for a pure confounding chromophore resembles the scaled 2nd derivative attenuation measurement for the pure analyte chromophore. For instance, consider hemoglobin oxygen saturation measurement (analyte chromophore) which exhibits a scaled 2nd derivative attenuation measurement that ranges from −1.5 to −2.0 for respective 50% and 90% hemoglobin oxygen saturation amounts. The wavelength gap for calculating the 2nd derivative attenuation values is chosen so that scaled 2nd derivative attenuation of water exhibits a similar scaled 2nd derivative value (i.e. −1.6). With a non-optimized wavelength gap the pure water scaled 2nd derivative attenuation value might be −3.0 or +1 which would result in a more significant analyte measurement error.

For the calibration relationship which relates a scaled 2nd derivative attenuation to a desired analyte, it is possible to use different wavelength gaps depending upon the range of analyte present. For instance, if the scaled 2nd derivative attenuation ranges from −1.0 to −1.5 for 0% and 50% hemoglobin oxygen saturation amounts, the amount of measurement error due to the confounding chromophore can be reduced by choosing a wavelength gap different than the higher hemoglobin oxygen saturation range (>50%) wavelength gap. In this case a wavelength gap which gives a pure water scaled 2nd derivative attenuation of −1.25 would further reduce measurement error specifically for low range hemoglobin oxygen saturation. A common theme is that a wavelength gap is chosen so that the ratio of the pure analyte or selected chromophore and pure confounding chromophore scaled 2nd derivative attenuation values resemble each other. To this end, it is desirable to use measurement wavelengths such that the numerator of the scaling function is a function of the selected analyte chromophore attenuation values taken near a local maximum along the second derivative attenuation curve while the denominator is near a local minimum of the selected analyte chromophore attenuation value taken along the second derivative attenuation curve. In the alternative, it is also possible for the numerator to be at a local minimum and the denominator to be at a local maximum for the second derivative attenuation curve. In another embodiment, after taking an initial reading at a first wavelength gap, a wavelength gap that is optimized for a specific range of hemoglobin concentrations is used thereafter.

All patents, patent applications, publications, references and documents referred to herein are hereby incorporated by reference herein as if fully disclosed in this application.

What is claimed is:

1. A method for reducing measurement error caused by water when determining the level of hemoglobin oxygenation in tissue, comprising the steps of:

illuminating the tissue under study using light emitted from a light source having at least the wavelengths of substantially 692 nm, 720 nm, 732 nm, 748 nm, 760 nm and 788 nm;

sensing light that has passed through a portion of the tissue, with a detector, at a predetermined distance from the source of the illumination, determining a value of attenuation of light at each of the wavelengths of illumination of the tissue; and with a processor:

determining a second derivative value of the light attenuation at 720 nm through the equation (Second Derivative Attenuation)$_{720}$=Attenuation$_{748}$−2(Attenuation$_{720}$)+Attenuation$_{692}$;

determining a second derivative value of the light attenuation at 760 nm through the equation (Second Derivative Attenuation)$_{760}$=Attenuation$_{788}$−2(Attenuation$_{760}$)+Attenuation$_{732}$;

determining a scaled (Second Derivative Attenuation)$_{720}$ as a function of the (Second Derivative Attenuation)$_{720}$ divided by the (Second Derivative Attenuation)$_{760}$; and comparing the scaled (Second Derivative Attenuation)$_{720}$ to stored data relating hemoglobin oxygenation to the scaled (Second Derivative Attenuation)$_{720}$ to determine the level of hemoglobin oxygenation.

2. A method for reducing measurement error caused by water when determining the level of hemoglobin oxygenation in tissue, comprising the steps of:
 illuminating the tissue under study using light emitted from a light source having at least the wavelengths of substantially 680 nm, 720 nm, 732 nm, 760 nm and 788 nm;
 sensing light that has passed through a portion of the tissue, with a detector, at a predetermined distance from the source of the illumination; and
 with a processor:
 determining a value of attenuation of light at each of the wavelengths of illumination of the tissue;
 determining a second derivative value of the light attenuation at 720 nm through the equation (Second Derivative Attenuation)$_{720}$=Attenuation$_{760}$−2(Attenuation$_{720}$)+Attenuation$_{680}$;
 determining a second derivative value of the light attenuation at 760 nm through the equation (Second Derivative Attenuation)760=Attenuation$_{788}$−2(Attenuation$_{760}$)+Attenuation$_{732}$;
 determining a scaled (Second Derivative Attenuation)$_{720}$ as a function of the (Second Derivative Attenuation)720 divided by the (Second Derivative Attenuation)$_{760}$; and
 comparing the scaled (Second Derivative Attenuation)$_{720}$ to stored data relating hemoglobin oxygenation to the scaled (Second Derivative Attenuation)$_{720}$ to determine the level of hemoglobin oxygenation.

3. A method for reducing measurement error caused by water when determining the level of hemoglobin oxygenation in tissue, comprising the steps of:
 illuminating the tissue under study using light emitted from a light source having at least the wavelengths of substantially 680 nm, 720 nm, 760 nm and 890 nm;
 sensing light that has passed through a portion of the tissue, with a detector, at a predetermined distance from the source of the illumination; and
 with a processor:
 determining a value of attenuation of light at each of the wavelengths of illumination of the tissue;
 determining a second derivative value of the light attenuation at 720 nm through the equation (Second Derivative Attenuation)$_{720}$=Attenuation$_{760}$−2(Attenuation$_{720}$)+Attenuation$_{680}$;
 determining a second derivative value of the light attenuation at 760 nm through the equation (Second Derivative Attenuation)$_{760}$=Attenuation$_{890}$−2(Attenuation$_{760}$)+Attenuation$_{720}$;
 determining a scaled (Second Derivative Attenuation)$_{720}$ as a function of the (Second Derivative Attenuation)$_{720}$ divided by the (Second Derivative Attenuation)$_{760}$; and
 comparing the scaled (Second Derivative Attenuation)$_{720}$ to stored data relating hemoglobin oxygenation to the scaled (Second Derivative Attenuation)$_{720}$ to determine the level of hemoglobin oxygenation.

4. A method for determining the level of hemoglobin oxygenation in tissue with at least one confounding chromophore present in the tissue under study, comprising the steps of:
 illuminating the tissue under study using light emitted from a light source at wavelengths such that scaled 2nd derivative attenuation measurement for the confounding chromophore is substantially similar to the scaled 2nd derivative attenuation measurement for the hemoglobin, wherein the wavelengths include 720 nm and 760 nm;
 sensing light that has passed through a portion of the tissue, with a detector, at a predetermined distance from the source of the illumination; and
 with a processor:
 determining a value of attenuation of light at each of the wavelengths of illumination of the tissue;
 determining a second derivative value of the light attenuation at 720 nm, determining a second derivative value of the light attenuation at 760 nm;
 determining a scaled (Second Derivative Attenuation)$_{720}$ as a function of the (Second Derivative Attenuation)$_{720}$ divided by the (Second Derivative Attenuation)$_{760}$; and
 comparing the scaled (Second Derivative Attenuation)$_{720}$ to stored data relating hemoglobin oxygenation to the scaled (Second Derivative Attenuation)$_{720}$ to determine the level of hemoglobin oxygenation.

5. The method of claim 4, wherein a wavelength gap between wavelengths used in the illuminating step is dependent upon a hemoglobin oxygenation level.

6. The method of claim 4, wherein a first wavelength gap between wavelengths is used in the illuminating step to determine an initial hemoglobin oxygenation level and a second wavelength gap, dependent upon the initial hemoglobin oxygenation level, is used thereafter.

7. The method of claim 4, wherein the confounding chromophore is water and the method includes reducing measurement error caused by water by using light at wavelengths such that scaled 2nd derivative attenuation measurement for the water is substantially similar to the scaled 2nd derivative attenuation measurement for the hemoglobin.

8. A method for determining the level of a selected chromophore in tissue with at least one confounding chromophore present in the tissue under study, comprising the steps of:
 illuminating the tissue under study using light emitted from a light source at wavelengths such that scaled 2nd derivative attenuation measurement for the confounding chromophore is substantially similar to the scaled 2nd derivative attenuation measurement for the selected chromophore wherein there is light at least first and second wavelengths;
 sensing light that has passed through a portion of the tissue, with a detector, at a predetermined distance from the source of the illumination; and
 with a processor:
 determining, a value of attenuation of light at each of the wavelengths of illumination of the tissue;
 determining a second derivative value of the light attenuation at the first wavelength,
 determining a second derivative value of the light attenuation at the second wavelength;
 determining a scaled Second Derivative Attenuation at the first wavelength as a function of the Second Derivative Attenuation at the first wavelength and the Second Derivative Attenuation at the second wavelength; and
 comparing the scaled Second Derivative Attenuation to stored data relating hemoglobin oxygenation to the scaled Second Derivative Attenuation at the first wavelength to determine the level of hemoglobin oxygenation.

9. The method of claim 8, wherein the first wavelength of light is selected so that the second derivative attenuation of the selected chromophore at the first wavelength is near either a local minimum or maximum and the second wavelength of light is selected so that the second derivative attenuation of the selected chromophore is the other of the local minimum or maximum.

10. The method of claim 8, wherein a wavelength gap between wavelengths used in the illuminating step is dependent upon a hemoglobin oxygenation level.

11. The method of claim 10, wherein a first wavelength gap between wavelengths is used in the illuminating step to determine an initial hemoglobin oxygenation level and a second wavelength gap, dependent upon the initial hemoglobin oxygenation level, is used thereafter.

12. The method of claim 8, wherein the confounding chromophore is water and the method includes reducing measurement error caused by water by using light at wavelengths such that scaled 2nd derivative attenuation measurement for the water is substantially similar to the scaled 2nd derivative attenuation measurement for the selected chromophore.

13. A measurement system for determining a relative concentration of a first form of a chromophore in a tissue sample also having a confounding chromophore, said chromophore comprising at least a first form and a second form, comprising:
(a) means for irradiating said tissue sample with at least first and second wavelengths of light such that scaled 2nd derivative attenuation measurement for the confounding chromophore is substantially similar to the scaled 2nd derivative attenuation measurement for the selected chromophore;
(b) means for detecting the spectral data emitted from said tissue;
(c) means for determining a first 2d derivative spectrum value of the spectral data at a first wavelength within said wavelength range at which the first 2d derivative spectrum value varies with the concentration of the first form of the chromophore;
(d) means for determining a second 2d derivative spectrum value of the spectral data at a second wavelength within said wavelength range at which the second 2d derivative spectrum value varies with a concentration of at least a second form of the chromophore;
(e) means for deriving a scaled, 2d derivative spectrum value from information comprising the first and second 2d derivative spectrum values; and
(f) means for storing a correlation which provides the relative chromophore concentration as a function of the scaled, 2d derivative spectrum value; and
(g) means for determining the relative concentration of the first form of the chromophore in the tissue sample from information comprising the scaled, 2d derivative spectrum value and the correlation.

14. The system of claim 13, wherein the first wavelength of light is selected so that the second derivative attenuation of the selected chromophore at the first wavelength is near either a local minimum or maximum and the second wavelength of light is selected so that the second derivative attenuation of the selected chromophore is the other of the local minimum or maximum.

15. The measurement system of claim 13 wherein said means for storing said correlation is a computer memory.

16. The measurement system of claim 13 wherein said means for determining said relative concentration is a computer.

17. The measurement system of claim 13, wherein a wavelength gap between wavelengths used is dependent upon a hemoglobin oxygenation level.

18. The measurement system of claim 13, wherein a first wavelength gap between wavelengths is used to determine an initial hemoglobin oxygenation level and a second wavelength gap, dependent upon the initial hemoglobin oxygenation level, is used thereafter.

19. The system of claim 13, wherein the confounding chromophore is water and the system includes a means for irradiating said tissue sample with at least first and second wavelengths of light such that scaled 2nd derivative attenuation measurement for the water is substantially similar to the scaled 2nd derivative attenuation measurement for the first form of the chromophore.

20. A system for measuring a relative concentration of a chromophore in a tissue sample which also contains a confounding chromophore, said chromophore comprising at least a first form and a second form, comprising:
(a) a memory comprising data representative of a correlation which provides the relative concentration of the first chromophore as a function of a scaled, 2d derivative spectrum value input, wherein the scaled second derivative spectrum value input is derived from a spectral response obtained from the tissue sample using light at first and second wavelengths such that scaled 2nd derivative attenuation measurement for the confounding chromophore is substantially similar to the scaled 2nd derivative attenuation measurement for the first chromophore;
(b) a light source assembly for generating spectroscopic radiation for irradiating the tissue sample;
(c) a spectroscopic detector for detecting the spectral response emitted by the tissue sample responsive to irradiation with the spectroscopic radiation; and
(d) a control system interfaced with the memory and the spectroscopic detector such that:
(i) the control system generates the scaled, second derivative spectrum value of the tissue sample from information comprising the spectral response of the tissue sample; and
(ii) the control system generates information representative of the relative concentration of the first form of the chromophore in the tissue sample from information comprising the scaled, second derivative spectrum value and the correlation provided in the memory.

21. The system of claim 20, wherein the first wavelength of light is selected so that the second derivative attenuation of the selected chromophore at the first wavelength is near either a local minimum or maximum and the second wavelength of light is selected so that the second derivative attenuation of the selected chromophore is the other of the local minimum or maximum.

22. The system of claim 20, wherein the scaled, 2d derivative spectrum value is obtained from the tissue sample in vivo.

23. The system of claim 20, wherein the spectroscopic radiation is near infrared radiation.

24. The system of claim 20, wherein the light source comprises individual light sources at 680, 720, 760 and 890 nm.

25. The system of claim 20, wherein the light source comprises individual light sources at 692, 720, 732, 748, 760 and 788 nm.

26. The system of claim 20, wherein the light source comprises individual light sources at 680, 720, 732, 760 and 788 nm.

27. The system of claim 20, wherein a wavelength gap between wavelengths used is dependent upon a hemoglobin oxygenation level.

28. The system of claim 20, wherein a first wavelength gap between wavelengths is used to determine an initial hemoglobin oxygenation level and a second wavelength gap, dependent upon the initial hemoglobin oxygenation level, is used thereafter.

29. The system of claim 20, wherein the confounding chromophore is water and the scaled second derivative spectrum value input is derived from a spectral response obtained from the tissue sample using light at first and second wavelengths such that scaled 2nd derivative attenuation measurement for the water is substantially similar to the scaled 2nd derivative attenuation measurement for the first chromophore.

* * * * *

UNITED STATES PATENT AND TRADEMARK OFFICE
CERTIFICATE OF CORRECTION

PATENT NO.       : 7,613,489 B2
APPLICATION NO. : 11/131698
DATED            : November 3, 2009
INVENTOR(S)      : Dean E. Myers It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1145 days.

Signed and Sealed this

Fourteenth Day of December, 2010

David J. Kappos
*Director of the United States Patent and Trademark Office*